(12) United States Patent
Aurrand-Lions et al.

(10) Patent No.: US 9,107,936 B2
(45) Date of Patent: Aug. 18, 2015

(54) ANTAGONISTS OF GRASP55 FOR USE AS A MEDICAMENT

(75) Inventors: Michel Aurrand-Lions, Marseilles (FR); Ana Zarubica, Marseilles (FR)

(73) Assignees: Institut National de la Sante et de la Recherche Medicale (INSERM), Paris (FR); Universite de la Mediterranee Aix-Marseille II, Marseilles (FR)

( * ) Notice: Subject to any disclaimer, the term of this patent is extended or adjusted under 35 U.S.C. 154(b) by 35 days.

(21) Appl. No.: 13/983,417

(22) PCT Filed: Feb. 2, 2012

(86) PCT No.: PCT/EP2012/051793
§ 371 (c)(1),
(2), (4) Date: Aug. 2, 2013

(87) PCT Pub. No.: WO2012/104386
PCT Pub. Date: Aug. 9, 2012

(65) Prior Publication Data
US 2013/0309252 A1 Nov. 21, 2013

(51) Int. Cl.
*C12N 15/11* (2006.01)
*A61K 31/713* (2006.01)
*C07K 14/47* (2006.01)
*C12N 15/113* (2010.01)
*A61K 39/395* (2006.01)
*C07H 21/04* (2006.01)

(52) U.S. Cl.
CPC ........... *A61K 31/713* (2013.01); *A61K 39/3955* (2013.01); *C07K 14/47* (2013.01); *C12N 15/113* (2013.01); *C12N 2310/14* (2013.01); *C12N 2310/531* (2013.01)

(58) Field of Classification Search
None
See application file for complete search history.

(56) References Cited

FOREIGN PATENT DOCUMENTS

WO 2005/032495 A2 4/2005
WO WO 2008038127 A2 * 4/2008

OTHER PUBLICATIONS

Zarubica et al., The golgi-associated protein GRASP55 is required for junctional adhesion molecule JAM-C protein stability and intracellular sorting, Dec. 15, 2010, Molecular Biology of the Cell, vol. 21, No. 24, abstract No. 1377/B676.*
Roghi et al., "Golgi reassembly stacking protein 55 interacts with membrane-type (MT) 1-matrix metalloprotease (MMP) and furin and plays a role in the activation of the MT1-MMP zymogen", FEBS Journal, Aug. 1, 2010, pp. 3158-3175, vol. 277, No. 15.
Tenan et al., "Cooperative expression of junctional adhesion molecule-C and -B supports growth and invasion of glioma", GLIA, Apr. 2010, pp. 524-537, vol. 58, No. 5.
Vinke et al., "The multiple facets of the Golgi reassembly stacking proteins", Biochemical Journal, Feb. 1, 2011, pp. 423-433, vol. 433, No. 3.
Novus Biologicals, "GRASP55 RNAi (H00026003-R01) Datasheet Novus Biologicals", Jun. 15, 2011, pp. 1-4, Web.

* cited by examiner

*Primary Examiner* — Dana Shin
(74) *Attorney, Agent, or Firm* — Whitham Curtis Christofferson & Cook, PC

(57) ABSTRACT

The present invention concerns antagonists of the Golgi reassembly-stacking protein of 55 k Da (Grasp55), for use as a medicament, in particular for use in the treatment of cell adhesion molecules implicated diseases, notably, MCAM or JAMs implicated diseases. According to some embodiments, said antagonists of the Golgi reassembly-stacking protein of 55 k Da (Grasp55) may be used in the treatment of cancer, metastases, and inflammatory diseases. The present invention further provides methods for screening for compounds liable of treating or preventing such diseases.

6 Claims, 13 Drawing Sheets

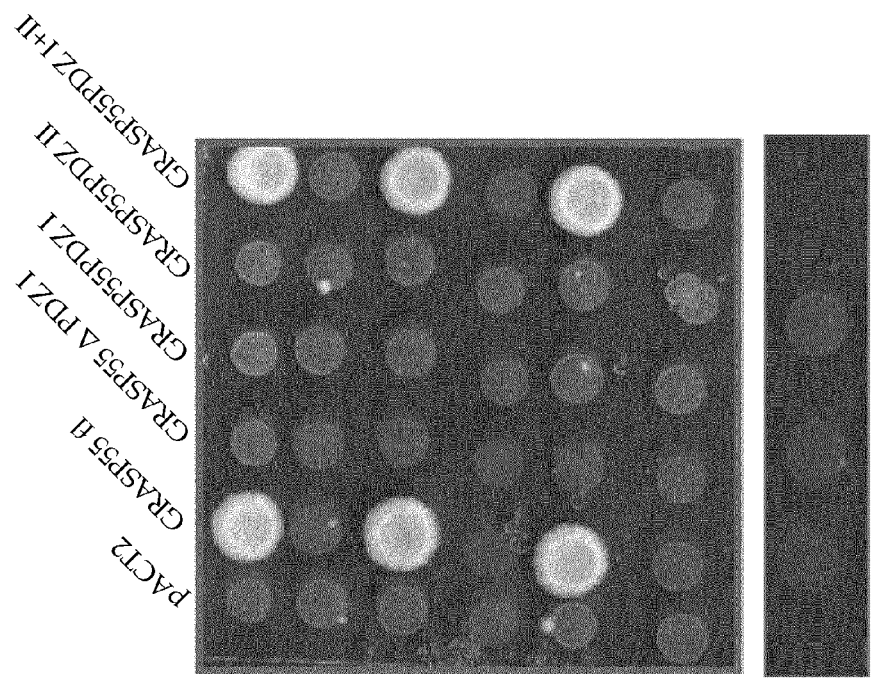
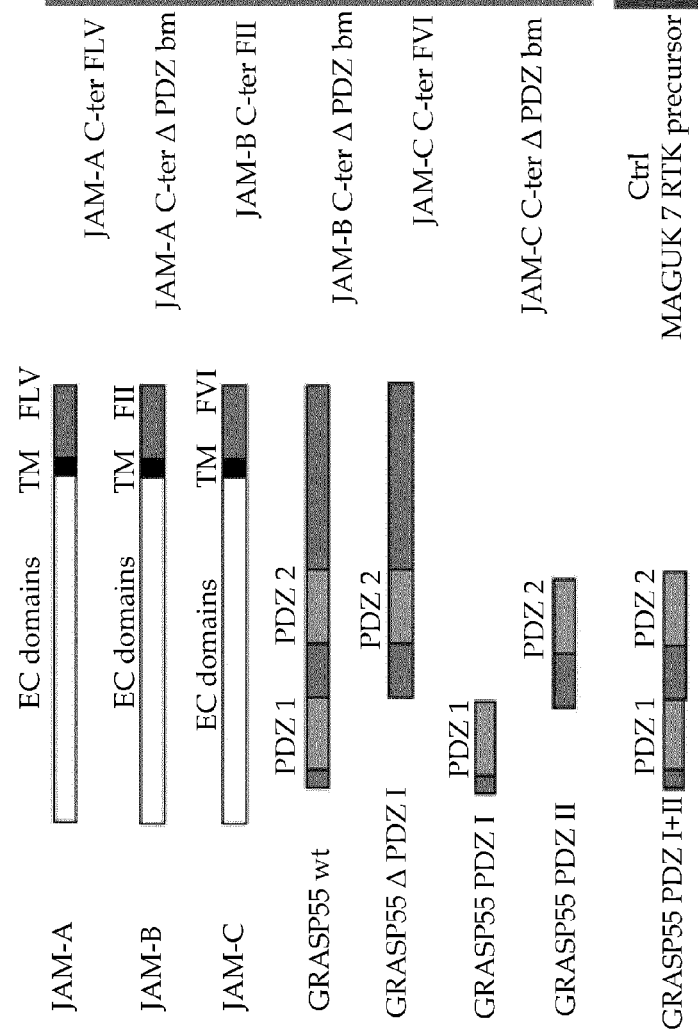
FIG.2

FIG.9

Peptides used for pull-down

| | | | |
|---|---|---|---|
| (SEQ ID NO:26) | JAM-A | Biotin- | SQPSTRSEGEFKQTSSFLV -COOH |
| (SEQ ID NO:27) | JAM-AΔ | Biotin- | SQPSTRSEGEFKQTSS -COOH |
| (SEQ ID NO:28) | JAM-B | Biotin- | SKVTTMSENDFKHTKSFII -COOH |
| (SEQ ID NO:29) | JAM-BΔ | Biotin- | SKVTTMSENDFKHTKS -COOH |
| (SEQ ID NO:30) | JAM-C | Biotin- | NYIRTSEEGDFRHKSSFVI -COOH |
| (SEQ ID NO:31) | JAM-CΔ | Biotin- | NYIRTSEEGDFRHKSS -COOH |

Consensus  NQPSTMSENDFKQTKSFII (SEQ ID NO:32)
          SKVT-RE-GE-RHKS--LV (SEQ ID NO:33)
          -YIR-S---------V-  (SEQ ID NO:34)
          ----*-**-**

```
hu JAM-A ...WFAYSRGHFDRTKKG--TS--SKVIYSQPSARSEGEFKQTSSFLV (SEQ ID NO:35)
mo JAM-A ...WFAYSRGYFETTKKG--TAP--GKVIYSQPSTRSEGEFKQTSSFLV (SEQ ID NO:36)
hu JAM-B ...CYAQRKGYFS--KET--SFQ--KSNSSSKATTMSENDFKHTKSFII (SEQ ID NO:37)
mo JAM-B ...CYAQRKGYFS--KET--SFQ--KGSPASKVTTMGENDFRHKSFII (SEQ ID NO:38)
hu JAM-C ...CCAYRRGYFINNKQDGESYKNPGKPDGVNYIRTDEEGDFRHKSSFVI (SEQ ID NO:39)
mo JAM-C ...CCAYRRGCFISSKQDGESYKSPGKHDGVNYIRSEEGDFRHKSSFVI (SEQ ID NO:40)
             **   *  ***  *    ****                PDZ bm
```

```
  1 MGSSQSVEIPGGGTEGYHVLRVQENSPGHRAGLEPFFDFIVSINGSRLNKDNDTLKDLLK
  1 MGSSQSVEIPGGGTEGYHVLRVQENSPGHRAGLEPFFDFIVSINGSRLNKDNDTLKDLLK
    ************************************************************

61 ANVEKPVKMLIYSSKTLELRETSVTPSNLWGGQGLLGVSIRFCSFDGANENVWHVLEVES
 61 ANVEKPVKMLIYSSKTLELREASVTPSNLWGGQGLLGVSIRFCSFDGANENVWHVLEVES
    ******************** ***************************************

121 NSPAALAGLRPHSDYIIGADTVMNESEDLFSLIETHEAKPLKLYVYNTDTDNCREVIITP
121 NSPAALAGLRPHSDYIIGADTVMNESEDLFSLIETHEAKPLKLYVYNTDTDNCREVIITP
    ************************************************************

181 NSAWGGEGSLGCGIGYGYLHRIPTRPFEEGKKISLPGQMAGTPITPLKDGFTEVQLSSVN
181 NSAWGGEGSLGCGIGYGYLHRIPTRPFEEGKKISLPGQMTGTPITPLKDGFTEVQLSSVS
    *************************************** *******************

241 PPSLSPPGTTGIEQSLTGLSISSTPPAVSSVLSTGVPTVPLLPPQVNQSLTSVPPMNPAT
241 PPSLSPPGTTGVEQSLSGLSISSAPPAVSNVLSTGVPTVPLLPPQVNQSLASMPPMNPAT
    *********** **** ****** ***** ******************** * *******

301 TLPGLMPLPAGLPNLPNL----NLNLPAPHIMPGVGLPELVNPGLPPLPSMPPRNLPGIA
301 TLPSLMPLSAGLPSLPNLPSLNFNLPAPHIMPGVGLPELGSPGLPPLPSLPPRNLPGIA
    *** **** **** ****     ***************    ******** ********

357 PLPLPSEFLPSFPLVPESSSAASSGELLSSLPPTSNAPSDPATTTAKADAASSLTVDVTP
361 PLPMLSDFLPSFPLVPEGSSAASAGEPLSSLP-AMGPPSDPVMTTAKADA-SSLTVDVTS
    *** * ********** ***** ** *****   ** **** ******* ********

417 PTAKAPTTVEDRVGDSTPVSEKPVSAAVDANASESP  (SEQ ID NO: 2)
419 PASKVPTTVEDRVSDCTPVEKPVS---DADASEPS   (SEQ ID NO: 1)
    *  * ******** ** ****  ****   ** ***
```

FIG.10

ANTAGONISTS OF GRASP55 FOR USE AS A MEDICAMENT

The present invention concerns antagonists of the Golgi reassembly-stacking protein of 55 kDa (Grasp55), for use as a medicament, in particular for use in the treatment of cell adhesion molecules implicated diseases, notably, MCAM or JAMs implicated diseases. According to some embodiments, said antagonists of the Golgi reassembly-stacking protein of 55 kDa (Grasp55) may be used in the treatment of cancer, metastases, and inflammatory diseases. The present invention further provides methods for screening for compounds liable of treating or preventing such diseases.

The Grasp55 protein is a medial Golgi protein that plays a role in assembly of the Golgi apparatus, vesicles tethering and mitotic progression and that has been involved in the intracellular transport of Acyl-CoA binding protein, CD8α, TGF-α and Frizzled-4 (for review: Vinke F P, Grieve A G, Rabouille C. Biochem J. 2011 Feb. 1; 433(3):423-33. Review.). It has been reported that GRASP55 interacts with MT1MMP in HT1080 tumor cells and affects its proteinase activity. At the same time, GRASP55 interacts with furin, PC5/6B and PC7, which are involved in pro-MT1-MMP activation. However, no study reports or suggests that Grasp55 may play a role in cancer or inflammatory diseases.

In contrast to that, CAMs notably MCAM and JAMs are known to be involved in cancer or inflammatory diseases. More particularly, it has been shown that surface shedding of JAM-C by metalloproteinases (ADAM proteins) is responsible for the sustained angiogenesis observed in chronic inflammatory disease such as arthritis. Moreover, it has been also shown that increased JAM-C expression is correlated with increased metastatic potential of spontaneous cancer cell variants notably in fibrosarcoma and melanomas. This is also the case for JAM-A in breast cancer or CD146 in melanomas. (Conn E M et al. J Biol Chem. 2008 Sep. 26; 283(39):26518-27; Fuse C et al. J Biol Chem. 2007 Mar1 6; 282(11):8276-83; Lamagna et al. Cancer Res. 2005. 65:5703-5710). This is in agreement with previous studies showing that over-expression of JAM-C is correlated with increased migration of glioblastoma and lung carcinoma cells, and that blocking JAM-C interaction with its ligand JAM-B inhibits angiogenesis, tumor growth and invasion (Mandicourt G, et al., J Biol Chem. 2007 Jan. 19; 282(3):1830-7; Tenan M, et al. Glia. 2010 April; 58(5):524-37; Reynolds L E, et al. Nature. 2010 Jun. 10; 465(7299):813-7; Imhof et al. J Pathol. 2007. 212: 198-208; Ody et al. Leukemia. 2007 21:1285-1293; U.S. Pat. No. 7,642,341; US 2010/034737; WO 03/106647; WO 2006/084078). It has thus been proposed that inhibiting JAM-B or JAM-C allows treating cancer and inflammatory diseases.

However, the adhesion molecules JAM-B and JAM-C discovered more than ten years ago, have been described as regulating the biology of platelets, endothelial and hematopoietic cells together with JAM-A. The JAM family members encompass two extracellular Ig domains of V and C2 type, a single transmembrane region, and a short cytoplasmic domain ending with a PDZ binding motif at the C-terminus. Previous art has thus proposed that inhibiting interaction of JAM-C with JAM-B will allow treating cancer and inflammatory diseases by means of mAbs directed against JAM-C and blocking interaction with JAM-B (WO2008/038127, WO2005/050213). However, since JAM-A and JAM-C are expressed on human platelets, the expression pattern may possibly lead to failure of extracellular domains targeting molecules. (Langer H F, et al., Arterioscler Thromb Vasc Biol. 2007; 27:1463-1470; Naik M U, et al. Blood. 2012, January 23; Santoso S, et al. J Exp Med. 2002; 196:679-691; Sobocka M B, et al., Blood. 2000; 95:2600-2609) Moreover, the use of antibodies targeting extracellular domains of these proteins may not be suited for treatment of patients due to side effects of antibodies on human platelets. This is especially true for patients suffering from cancer and inflammatory diseases in which the risk of disseminated intravascular coagulation syndrome is high. This includes patient with severe inflammation, hematologic malignancies or metastatic cancers with high risk of disseminated intravascular coagulation (Franchini M, et al. Semin Thromb Hemost. 2010; 36:388-403; Levi M, et al. Semin Thromb Hemost. 2010; 36:367-377; Pinto F, et al. Arch Ital Urol Androl. 2009; 81:212-214) for which it will be indicated to inhibit JAM-A and JAM-C expression or release by other means than using reagents targeting the extracellular domain of the JAMs that could contribute to platelet activation (i.e. antibodies against JAM-A or JAM-C).

Cancer is one the major health problems in developed countries today. Cancer is an unregulated proliferation of cells due to loss of normal controls, resulting in unregulated growth, lack of differentiation, local tissue invasion, and, often, metastasis. Cancer can develop in any tissue or organ at any age.

Some cancers are curable if detected at an early stage, and long-term can also be possible in later stages. However, cure is not always possible and is not attempted in some advanced cases in which palliative care provides better quality of life than aggressive treatment, particularly in the elderly or in patients with underlying comorbid disorders.

In addition, some cancers are difficultly or not curable for the time being. For example, the overall prognosis for lung cancer is poor. The median survival time for limited-stage small cell lung carcinoma (SCLC) is 20 months, with a 5-years survival rate of 20%. Patients with extensive-stage SCLC do especially poorly, with a 5-years survival rate inferior to 1%.

In addition, numerous model systems suggest that ADAM proteins, such as ADAM-10 and ADAM-17, are causally involved in tumor formation/progression. In human cancer, specific ADAMs are up-regulated, with levels generally correlating with parameters of tumor progression and poor outcome. In preclinical models, selective ADAM inhibitors against ADAM-10 and ADAM-17 have been shown to synergize with existing therapies in decreasing tumor growth. The ADAM proteins are considered as potential targets for the treatment of cancer, especially malignancies that are dependent on human epidermal growth factor receptor ligands or tumor necrosis factor-α. However, ADAMs inhibitors have numerous sides' effects.

Therefore, there is a need in the art for compounds capable of treating cancers, in particular of cancers for which no efficient treatment exists for the time being.

Treatment of inflammatory diseases is another major issue in the field of medicine. Indeed, inflammation is a symptom that is present in vast variety of human diseases. Therefore, there is also a need in the art for compounds capable of treating inflammatory diseases.

DESCRIPTION OF THE INVENTION

The inventors have unexpectedly found that JAM-B interacts with Grasp55. Using biochemistry and yeast two hybrid system, a direct interaction between Grasp55 and JAM-A, JAM-B and JAM-C was demonstrated. In addition, an interaction between Grasp55 and CD146 was found using co-immunoprecipitation assays.

The inventors have found that these interactions are mediated through the GRASP55 PDZ motifs preferably through the first GRASP55 PDZ motif (called herein after PDZ1 domain and comprised in PDZI+II and PDZI' fragments) and intracellular C-termini motifs of these proteins.

The inventors hypothesized that Grasp55 is an intracellular adapter regulating both the transport of JAM proteins to the cell surface and their release from the cell surface. To test this hypothesis, the inventors identified the minimal domain of Grasp55 necessary for its interaction with JAM-A, JAM-B and JAM-C to be PDZI' fragment. The biological effect of Grasp55 silencing in endothelial and tumor cells was then assessed. As a paradigm, cells were depleted of Grasp55 expression by means of siRNAs and shRNAs and the consequences on JAM-C expression and release were evaluated. It was found that silencing Grasp55 expression decreases the expression of the adhesion molecule JAM-C as well as its release from tumor and inflammatory endothelial cells, and also diminishes tumor cell migration.

In vivo experiments were carried out in mice, and it was found that silencing Grasp55 allows reducing the development of lung metastasis.

Therefore, the inventors have shown that Grasp55 antagonists can be used to treat cell adhesion molecules implicated diseases, notably, MCAM or JAMs implicated diseases. According to some embodiments, the inventors have shown that Grasp55 antagonists can be used to treat cancer, metastases, and inflammatory disease more particularly adhesion molecule release from inflammatory endothelial cells, cell adhesion molecules implicated cancers such as CD146 or JAMs implicated cancers. Such antagonists are believed to be particularly advantageous since the survival of cell lines silenced for Grasp55 expression demonstrates that the functional inhibition of Grasp55 is not toxic. In addition, the present antagonists represent a major technical improvement to the approaches involving molecules targeting extracellular domains of JAMs. Indeed, JAM-A and JAM-C are heavily expressed on the surface of human platelets, rendering the use of antagonists against extracellular JAM-A and JAM-C domains that can induce platelets activation or aggregation difficult.

The inventors developed ELISA and HTRF assays to measure Grasp55/JAM-C interaction. These assays are optimal tools for drug screening. Indeed, they allow screening for compounds expected to inhibit cell surface protein expression (in particular JAM expression) without the use of extracellular targeting molecules.

Finally, the inventors have shown that Grasp55 is implicated in the regulatory functions of ADAM-10 and ADAM-17 on JAM-A and JAM-C release and thus that the Grasp55 antagonists may be an advantageous alternative to ADAMs inhibitors in treating cell adhesion molecules implicated diseases and notably cell adhesion molecules implicated cancer or inflammation diseases.

Antagonists of Grasp55 for Use as a Medicament

The inventors have found that Grasp55 antagonists are capable of decreasing the expression of the adhesion molecule JAM-C as well as its release. Grasp55 antagonists are thus believed to be capable of treating or preventing cell adhesion molecules implicated diseases, notably, CD146 or JAMs implicated diseases, cancer, inflammatory diseases, and of inhibiting angiogenesis. According to some embodiments, the Grasp55 antagonists are thus believed to be capable of treating or preventing adhesion molecule release from inflammatory endothelial cells, cell adhesion molecules implicated cancers such as CD146 or JAMs implicated cancers. In addition, the inventors have demonstrated that such antagonists allow reducing the development of lung metastasis in vivo.

Therefore, the present invention provides an antagonist of the Golgi reassembly-stacking protein of 55 kDa (Grasp55), for use as a medicament. More specifically, the present invention provides an antagonist of Grasp55 for use in the treatment or the prevention of cell adhesion molecules implicated diseases, notably, CD146 or JAMs implicated diseases or a disease selected from the group consisting of cancer, metastases, and inflammatory diseases. According to some embodiments, the present invention provides an antagonist of Grasp55 for use in the treatment or the prevention of adhesion molecule release from inflammatory endothelial cells, cell adhesion molecules implicated cancers such as CD146 or JAMs implicated cancers The invention further provides a method for treating a patient suffering from cell adhesion molecules implicated diseases, notably, CD146 or JAMs implicated diseases said method comprising the step of administering an effective amount of an antagonist of Grasp55 to an individual in need thereof.

As used herein, the term "adhesion molecules" or "CAM" or "cell adhesion molecules" refers to proteins located on the cell surface involved in the binding with other cells or with the extracellular matrix (ECM) such as JAMs proteins or melanoma cell adhesion molecule (MCAM).

As used herein, the term "cell adhesion molecules implicated diseases" refers to any type of disease in which cell adhesion molecules are known or are described as being deregulated, over-expressed or under-expressed or as inducting or potentiating the pathogenesis or the pathological progression. As way of example, JAM-C and CD146 have been described as over-expressed in melanoma (Langer H F. et al., Cancer Res. 2011 Jun. 15; 71(12):4096-105; Zeng Q, et al., Proc Natl Acad Sci USA. 2011 Dec. 30). By the opposite, JAM-A has been described as under-expressed in breast cancers (Naik M U, et al., Cancer Res. 2008 Apr. 1; 68(7):2194-203). A "CAM implicated disease" may be a disease for which there are indications for treatment using antibodies inhibiting CAM activity. In a further aspect, the "CAM implicated disease" may be a disease in which deregulated expression of CAM expression is observed. For skilled in the art, this can be appreciated by CAM expression testing using flow-cytometry, immunohistochemistry, polymerase chain reaction, western blotting on pathological samples compared to healthy tissue.

In another aspect deregulation of CAMs could be appreciated by dosing soluble CAMs present in biological fluids such as synovial fluid, ascitis, serum, plasma, saliva, urina of patients as compared to healthy donors using ELISA, RIA, etc. . . .

In some embodiments, examples of such diseases may be cancer, metastases and inflammatory diseases.

As used herein, the term "MCAM or JAMs implicated diseases", "CD146 or JAMs implicated diseases" refers to any of disease in which MCAM (notably CD146) or JAMs proteins are known or are described as being deregulated or as inducting or potentiating the pathogenesis or the pathological progression. Examples of such diseases may be cancer, metastases, and inflammatory diseases. Indeed, CD146 and JAM-A are known to be associated with melanoma, breast cancer and colon carcinoma cell migration, while JAM-C has been associated with glioblastoma, lung carcinoma and fibrosarcoma cells migration.

As used herein, the terms "cell adhesion molecules implicated cancers", "MCAM or JAMs implicated cancers" or "CD146 or JAMs implicated cancers" refer to any of cancer or cancer stages in which cell adhesion molecules or MCAMs such as CD146 or JAMs proteins are known or are described as being deregulated or as inducing or potentiating the pathogenesis or the pathological progression. Notably, some cancer stages during pathological progression such as tumor growth, invasion or metastasis that involve specifically cell adhesion molecules.

The invention further provides a method for treating a patient suffering from a disease selected from the group consisting of cancer, metastases, and inflammatory disease, said method comprising the step of administering an effective amount of an antagonist of Grasp55 to an individual in need thereof.

In a first embodiment, the disease to be treated or prevented according to the invention is a cancer. As used herein, the term "cancer" refers to any type of malignant (i.e. non benign) tumor. The malignant tumor may correspond to a primary tumor or to a secondary tumor (i.e. a metastasis). Further, the tumor may correspond to a solid malignant tumor, which includes e.g. carcinomas, adenocarcinomas, sarcomas, melanomas, mesotheliomas, blastomas, or to a blood cancer such as leukaemias, lymphomas and myelomas. The cancer may for example correspond to a solid carcinoma, a melanoma, a lung cancer (including but not limited to non-small cell lung carcinomas (NSCLC), Small cell lung carcinoma (SCLC), combined small cell carcinomas, pleuropulmonary blastomas, carcinoid tumors, sarcomatoid carcinomas, carcinoid tumors, adenosquamous carcinomas, squamous cell lung carcinomas, adenocarcinomas and large cell lung carcinomas), a brain cancer (including but not limited to gliomas, glioblastomas, astrocytomas, oligoastrocytomas, oligodendrogliomas and ependymomas), kidney cancer, prostate cancer, breast cancer, myelodysplastic syndrome and leukemia.

Since the inventors have found that antagonists of Grasp55 decreases migration of melanoma in vitro (see FIG. 7) and reduces the development of lung metastasis in vivo (see FIG. 11), the cancer to be treated or preventing according to the invention preferably correspond to a secondary cancer (e.g. metastases), or a cancer known to have a high metastatic potential.

Also preferably, the invention is preferably directed to an antagonist of Grasp55 for use in the prevention of metastases.

In a second embodiment, the disease to be treated or prevented according to the invention is an inflammatory disease. As used herein, the term "inflammatory disease" refers to any disease in which there is an inflammation. Examples of inflammatory diseases include but are not limited to asthma, autoimmune diseases (e.g. rheumatoid arthritis, arteriosclerosis, Crohns disease, inflammatory bowel disease, lupus erythematosus, multiple sclerosis, etc.), chronic prostatitis, glomerulonephritis, pelvic inflammatory disease, reperfusion injury, Pancreatitis, transplant rejection, sarcoidosis, vasculitis, interstitial cystitis, allergies, inflammatory myopathies and infection.

As used herein, the term "Grasp55 antagonist" refers to a compound that inhibits or reduces Grasp55 biological activity. The biological activity of Grasp55 depends on the amount of the protein within the cells (i.e. its expression level) as well as on the activity of the protein. Therefore, the Grasp55 antagonist may reduce or inhibit either Grasp55 expression, or Grasp55 protein activity.

As used herein, the term "Golgi reassembly-stacking protein of 55 kDa", abbreviated 'Grasp55", encompasses any naturally occurring isoform of the Grasp55 protein, including the murine Grasp55 protein of SEQ ID NO: 1, the human Grasp55 protein of SEQ ID NO: 2, allelic variants thereof, splice variants thereof and homologous proteins in other species.

The skilled in the art can easily determine whether a compound is a Grasp55 antagonist. For example, the skilled in the art can assess whether a compound reduces or abolishes Grasp55 expression by Western Blotting or by RT-PCR. The biological activity of Grasp55 can also be measured by assessing the capacity of Grasp55 to bind to its natural binding partners such as JAM-A, JAM-B, JAM-C or CD146. The binding of Grasp55 to one of its binding partners may for example be assessed using the immunoprecipitation assay, the pull-down assay, the ELISA or HTRF assays or the yeast two hybrid system (Y2H) that are described in detail in the Examples of the present specification. A compound inhibiting binding of Grasp55 to at least one of JAM-A, JAM-B, JAM-C or CD146 is defined as a Grasp55 antagonist. Alternatively, the biological activity of Grasp55 can be determined through measure of soluble JAMs release, for example as described below in the Examples. A compound reducing or abolishing release of soluble JAM is defined as a Grasp55 antagonist.

In one embodiment, the antagonist is capable of reducing the amount of Grasp55 in cells. Preferably, such an antagonist is a nucleic acid targeting an mRNA encoding Grasp55.

As used herein, a nucleic acid that "targets" an mRNA refers to a nucleic acid that is capable of specifically binding to said mRNA. That is to say, the nucleic acid comprises a sequence that is at least partially complementary, preferably perfectly complementary, to a region of the sequence of said mRNA, said complementarity being sufficient to yield specific binding under intra-cellular conditions.

As immediately apparent to the skilled in the art, by a sequence that is "perfectly complementary to" a second sequence is meant the reverse complement counterpart of the second sequence, either under the form of a DNA molecule or under the form of a RNA molecule. A sequence is "partially complementary to" a second sequence if there are one or more mismatches.

Nucleic acids that target an mRNA encoding Grasp55 may be designed by using the sequence of said mRNA as a basis, e.g. using bioinformatic tools.

The nucleic acids according to the invention are capable of reducing the amount of Grasp in cells, e.g. in cancerous cells such as B16F10 mouse melanoma cells. Methods for determining whether a nucleic acid is capable of reducing the amount of Grasp55 are provided in the Examples.

The nucleic acids according to the invention may for example correspond to antisense oligonucleotides or to interfering RNAs (including siRNAs, shRNAs, miRNAs, dsRNAs, and other RNA species that can be cleaved in vivo to form siRNAs).

The nucleic acids for use according to the invention typically have a length of from 12 to 50 nucleotides, e.g. 12 to 35 nucleotides, from 12 to 30, from 12 to 25, from 12 to 22, from 15 to 35, from 15 to 30, from 15 to 25, from 15 to 22, from 18 to 22, or about 19, 20 or 21 nucleotides.

The nucleic acids for use according to the invention may for example comprise or consist of 12 to 50 consecutive nucleotides, e.g. 12 to 35, from 12 to 30, from 12 to 25, from 12 to 22, from 15 to 35, from 15 to 30, from 15 to 25, from 15 to 22, from 18 to 22, or about 19, 20 or 21 consecutive nucleotides of a sequence complementary to the mRNA encoding Grasp55.

The present invention provides several specific siRNAs and shRNAs acid targeting an mRNA encoding Grasp55 that have been shown to efficiently reducing the amount of Grasp55 in cells (see Examples 3 and 4).

Therefore, the nucleic acid for use according to the invention preferably comprises or consists of a fragment of at least 5, 8, 10, 12, 15, 18, 19, 20 or 21 nucleotides of any one of SEQ ID Nos. 6-10, 12 and 13 (either under DNA form, or under RNA form, or under a hybrid DNA/RNA form).

Also preferably, it may comprise or consist of the corresponding regions of a Grasp55 mRNA derived from another species (e.g. the corresponding region of a human Grasp55 mRNA). The corresponding region in another species can easily be identified by the skilled in the art by aligning the sequences of the Grasp55 mRNAs.

Most preferably, the nucleic acid targeting an mRNA encoding Grasp55 is an interfering RNA (iRNA).

The term "iRNA" include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the iRNA molecules of the present invention can also comprise non-standard nucleotides, including non-naturally occurring nucleotides or deoxyribonucleotides. Collectively, all such altered iRNA compounds are referred to as analogs or analogs of naturally-occurring RNA. iRNA of the present invention need only be sufficiently similar to natural RNA that it has the ability to mediate RNA interference. As used herein the phrase "mediate RNA Interference" refers to and indicates the ability to distinguish which mRNA are to be affected by the RNA interference machinery or process. RNA that mediates RNA interference interacts with the RNA interference machinery such that it directs the machinery to degrade particular mRNAs or to otherwise reduce the expression of the target protein. In one embodiment, the present invention relates to iRNA molecules that direct cleavage of specific mRNA to which their sequence corresponds. It is not necessary that there be perfect correspondence of the sequences, but the correspondence must be sufficient to enable the iRNA to direct RNA interference inhibition by cleavage or lack of expression of the target mRNA.

The iRNA molecules of the present invention may comprise an RNA portion and some additional portion, for example a deoxyribonucleotide portion. The total number of nucleotides in the RNA molecule is suitably less than 49 in order to be effective mediators of RNA interference. In preferred RNA molecules, the number of nucleotides is 16 to 29, more preferably 18 to 23, and most preferably 21-23.

As indicated above, the term "iRNA" includes but is not limited to siRNAs, shRNAs, miRNAs, dsRNAs, and other RNA species that can be cleaved in vivo to form siRNAs.

A "short interfering RNA" or "siRNA" comprises a RNA duplex (double-stranded region) and can further comprises one or two single-stranded overhangs, 3' or 5' overhangs.

A "short hairpin RNA (shRNA)" refers to a segment of RNA that is complementary to a portion of a target gene (complementary to one or more transcripts of a target gene), and has a stem-loop (hairpin) structure.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. One can design and express artificial miRNAs based on the features of existing miRNA genes. The miR-30 (microRNA 30) architecture can be used to express miRNAs (or siRNAs) from RNA polymerase II promoter-based expression plasmids (Zeng et al, 2005, Methods enzymol. 392:371-380). In some instances the precursor miRNA molecules may include more than one stem-loop structure. The multiple stem-loop structures may be linked to one another through a linker, such as, for example, a nucleic acid linker, a miRNA flanking sequence, other molecules, or some combination thereof.

The nucleic acids employed as antisense or iRNA molecules may be modified, preferably chemically modified, in order to increase the stability and/or therapeutic efficiency of the nucleic acids in vivo. For example, the nucleic acids may be employed as phosphorothioate derivatives (replacement of a non-bridging phosphoryl oxygen atom with a sulfur atom) which have increased resistance to nuclease digestion. MOE modification (ISIS backbone) is also effective.

In a specific embodiment, the nucleic acid for use according to the invention is:
a) a siRNA consisting of any one of SEQ ID Nos. 6-10;
b) a shRNA comprising a sequence of SEQ ID NO: 12 and a sequence of SEQ ID NO: 13;
c) a siRNA or a shRNA targeting the same region of the mRNA encoding Grasp55 as the siRNA of (a) or the shRNA of (b) (for example the same region in another species, especially in human).

In another embodiment, the antagonist is capable of inhibiting the interaction of Grasp55 with one of its binding partners, notably binding partners that specifically bind to at list on of Grasp55 PDZ domains such as the first PDZ domain of Grasp55 (from the N terminal extremity of Grasp55). Preferably, the antagonist is capable of inhibiting the interaction of Grasp55 with a junctional adhesion molecule (JAM) or a melanoma cell adhesion molecule (MCAM). As indicated here above, the skilled in the art can easily determine whether a compound is capable of inhibiting the interaction of Grasp55 with one of its binding partners using the methods provided herein.

Preferably, such a Grasp55 antagonist is capable of "specifically binding" to Grasp55. Methods for determining whether the antagonist is capable of specifically binding to Grasp55 are well-known to the skilled in the art. Such methods for example include dose response assays with a competitive ligand, co-immunoprecipitation, pull-down assays, surface plasmon resonance (e.g. using a BIACore), HTRF and yeast double-hybrid assays. Herein, the term "specific binding" to a protein has its usual meaning in the art, and is used to qualify a binding as opposed to a "non-specific binding".

As used herein, the term "melanoma cell adhesion molecule" or "MCAM" notably encompasses the CD146 proteins.

As used herein, the term "junctional adhesion molecule" or "JAM" notably encompasses the JAM-A, JAM-B and JAM-C proteins.

By "JAM-A" is meant any naturally occurring isoform of the JAM-A protein, including the murine JAM-A protein of SEQ ID NO: 3, the human JAM-A protein of SEQ ID NO: 23, allelic variants thereof, splice variants thereof and homologous proteins in other species.

By "JAM-B" is meant any naturally occurring isoform of the JAM-B protein, including the murine JAM-B protein of SEQ ID NO: 4, the human JAM-B protein of SEQ ID NO: 24, allelic variants thereof, splice variants thereof and homologous proteins in other species.

By "JAM-C" is meant any naturally occurring isoform of the JAM-B protein, including the murine JAM-C protein of SEQ ID NO: 5, the human JAM-C protein of SEQ ID NO: 25, allelic variants thereof, splice variants thereof and homologous proteins in other species.

Such an antagonist capable of inhibiting the interaction of Grasp55 with one of its binding partners can for example be selected from the group consisting of a small molecule, an antibody, an aptamer and a peptide.

Preferably, the antagonist is a chemical molecule, most preferably a small chemical molecule.

In the frame of a method of treatment or prevention, the antagonist is administered in an "effective amount" to a patient, i.e. in an amount sufficient to treat or prevent the disease. It will be appreciated that this amount will vary both with the effectiveness of the antagonist employed, and with the nature of any carrier used. The determination of appropriate amounts for any given composition is within the skill in the art, through standard series of tests designed to assess appropriate therapeutic levels.

The patient preferably is a human individual. However, the veterinary use of the antagonist according to the present invention is also envisioned. The patient may thus also correspond to a non-human individual, preferably a non-human mammal.

The term "treating" is meant a therapeutic method, i.e. a method aiming at curing, improving the condition and/or extending the lifespan of an individual suffering from a disease. By "preventing" is meant a prophylactic method, i.e. a method aiming at preventing the appearance of at least some of the symptoms of said disease (e.g. in the frame of cancer, the prevention includes reducing the risk of relapse and reducing the risk of appearance of metastases).

Grasp55 for Use as a Target

As indicated above, antagonists of Grasp55 are useful as medicaments for treating or preventing cell adhesion molecules implicated diseases, notably, CD146 or JAMs implicated diseases. More particularly, antagonists of Grasp55 are useful as medicaments for treating or preventing cell adhesion molecules implicated cancer or CD146 or JAMs implicated diseases. The present invention advantageously provides methods for identifying new antagonists of Grasp55. In particular, the inventors have found that a polypeptide comprising or consisting of amino acids 1 to 208, preferably, 1 to 160, more preferably 1 to 107 of murine Grasp55 can be used as a target for identifying Grasp55 antagonists.

Therefore, the present invention provides the use of Grasp55, or of a polypeptide comprising either amino acids 1 to 208, preferably, 1 to 160, more preferably 1 to 107 of murine Grasp55 or the corresponding region of a Grasp55 protein derived from another species, as a target for screening compounds liable to be medicaments, in particular compounds liable of treating or preventing a disease selected from the group consisting of cancer, metastases and an inflammatory disease.

More specifically, the present invention provides a method for screening for compounds liable to be medicaments, e.g. compounds liable of treating or preventing a disease selected from the group consisting of cell adhesion molecules implicated diseases, CD146 or JAMs implicated diseases, notably selected from the group consisting of cancer, metastases, and inflammatory disease, said method comprising the steps of:
 a) providing a first polypeptide that comprises either amino acids 1 to 208, preferably, 1 to 160, more preferably 1 to 107 of murine Grasp55 or the corresponding region of a Grasp55 protein derived from another species, or a cell expressing said first polypeptide;
 b) providing a second polypeptide that is a binding partner of Grasp55, or a cell expressing said second polypeptide;
 c) providing a candidate compound;
 d) determining whether said candidate compound is capable of inhibiting binding of said first polypeptide to said second polypeptide;
wherein the determination that said candidate compound is capable of inhibiting binding of the first polypeptide to the second polypeptide indicates that said candidate compound is a liable to be a medicament, e.g. a compound liable of treating or preventing cancer, metastases, and inflammatory disease.

Determining whether said candidate compound is capable of inhibiting binding of said first polypeptide to said second polypeptide typically comprises the following steps:
 i. assessing binding of the first polypeptide to the second polypeptide in the absence of the candidate compound;
 ii. assessing binding of the first polypeptide to the second polypeptide in the presence of the candidate compound;
 iii. comparing the results obtained at steps (i) and (ii);
whereby a reduced binding at step (ii), compared to the binding at step (i), indicates that candidate compound is capable of inhibiting binding of said first polypeptide to said second polypeptide;

As apparent to the skilled in the art, the above method is carried out in vitro.

By a compound "liable of" or "susceptible of" of treating or preventing a disease is meant a compound which is believed to be capable of treating or preventing said disease. Such a compound typically corresponds to a compound that is selected for preclinical or clinical trials in order to confirm its capacity to treat or prevent the disease. In the field of drug discovery, such compounds are sometimes referred to as "hits" or "leads".

The first polypeptide that is used in the method according to the invention comprises either amino acids 1 to 208, preferably, 1 to 160, more preferably 1 to 107 of murine Grasp55 (e.g. of SEQ ID NO: 1) or the corresponding region of a Grasp55 protein derived from another species. Indeed, the inventors have found that this region, which comprises the PDZ domain I and the PDZ domain II of Grasp55, is necessary and sufficient to sustain the interaction with Grasp55's binding partners.

The skilled in the art can easily determine the "corresponding region of a protein derived from another species" by carrying out a sequence alignment using, e.g. the alignment program of the ExPASY Proteomics server. For example, the region of human Grasp55 corresponding to amino acids 1 to 208, preferably, 1 to 160, more preferably 1 to 107 of murine Grasp55 is amino acids 1 to 208, preferably, 1 to 160, more preferably 1 to 107 of human Grasp55 (see the sequence alignment on FIG. 10).

Therefore, the first polypeptide may for example comprise or consist of:
 a) an amino acid sequence of SEQ ID NO: 1 (i.e. murine Grasp55);
 b) an amino acid sequence of SEQ ID NO: 2 (i.e. human Grasp55);
 c) amino acids 1 to 208, preferably, 1 to 160, more preferably 1 to 107 of SEQ ID NO: 1;
 d) amino acids 1 to 208, preferably, 1 to 160, more preferably 1 to 107 of SEQ ID NO: 2; or
 e) an amino acid sequence that is at least 80%, 85%, 90%, 95%, 96%, 97%, 98% or 99% identical to the sequence of any one of (a) to (d), provided said first polypeptide is biologically active (i.e. provided it retains the capacity of binding to at least one, preferably all, natural binding partner(s) of Grasp55).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the frame of the present application, the percentage of identity is calculated using a global alignment (i.e., the two sequences are compared over their entire length). Methods for comparing the identity and homology of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Mutants consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the mutant consisting of an amino acid sequence at least 80%, 85%, 90%, 95%, 96%, 97%, 98% or 99% identical to a reference sequence may correspond to a homologous sequence derived from another mammalian species than the reference sequence. In another preferred embodiment, the substitution preferably corresponds to a conservative substitution as indicated in the table below.

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

The second polypeptide is a binding partner of Grasp55. It may be a naturally-occurring binding partner of Grasp55, or a polypeptide comprising or consisting of a fragment thereof, provided that said fragment retains the capacity to bind to Grasp55. The binding partners may for example be selected from the group consisting of:
a) a polypeptide comprising or consisting of amino acids 260 to 299 of murine junctional adhesion molecule A (JAM-A) (e.g. of SEQ ID NO: 3), or the corresponding region of a JAM-A protein derived from another species;
b) a polypeptide comprising or consisting of amino acids 258 to 298 of murine junctional adhesion molecule B (JAM-B) (e.g. of SEQ ID NO: 4), or the corresponding region of a JAM-B protein derived from another species;
c) a polypeptide comprising or consisting of amino acids 263 to 310 of murine junctional adhesion molecule C (JAM-C) (e.g. of SEQ ID NO: 5), or the corresponding region of a JAM-C protein derived from another species;
d) a polypeptide comprising or consisting of the amino acid sequence of CD146, or a fragment thereof, provided that said fragment retains the capacity to bind to Grasp55;
e) a polypeptide comprising or consisting of amino acids 260 to 299 of human JAM-A (e.g. of SEQ ID NO: 23);
f) a polypeptide comprising or consisting of amino acids 260 to 298 of human JAM-B (e.g. of SEQ ID NO: 24);
g) a polypeptide comprising or consisting of amino acids 263 to 310 of human JAM-C (e.g. of SEQ ID NO: 25);
h) a polypeptide comprising or consisting of any one of SEQ ID Nos. 35 to 40; and
i) a polypeptide comprising or consisting of an amino acid sequence that is at least 80%, 85%, 90%, 95%, 96%, 97%, 98% or 99% identical to amino acids amino acids 260 to 299 of murine JAM-A, to amino acids amino acids 260 to 299 of human JAM-A, to amino acids 258 to 298 of murine JAM-B, to amino acids 260 to 298 of human JAM-B, to amino acids 263 to 310 of murine JAM-C, to amino acids 263 to 310 of human JAM-C, or to any one of SEQ ID Nos. 35 to 40;

By "CD146" also known as the melanoma cell adhesion molecule (MCAM) or cell surface glycoprotein MUC18, is a 113 kDa cell adhesion molecule. "CD146" is meant any naturally occurring isoform of the CD146 protein (also referred to as the Cell surface glycoprotein MUC18), including the murine CD146 protein, the human CD146 protein, allelic variants thereof, splice variants thereof and homologous proteins in other species. The sequence of human CD146 is for example shown in UniProtKB database accession No. P43121 (Version No. 103 dated Nov. 30, 2010).

Determining whether the candidate compound is capable of inhibiting binding of said first polypeptide to said second polypeptide can for example be done using any of the protocols described in detail in the examples, e.g. through immunoprecipitation and Western blotting, flow cytometry, a yeast two-hybrid assay or an ELISA assay.

In a preferred embodiment of the screening method according to the invention, the step of determining whether said candidate compound is capable of inhibiting binding of the first polypeptide to the second polypeptide is carried out through ELISA or HTRF assays. Indeed, such assays are particularly suitable for performing a high-throughput screening (HTS). In addition, it is fast, accurate, and allows a direct measure of the interaction.

More particularly, the inventors have set up the following assay (see Example 5). Briefly, the first polypeptide, which comprises Grasp55 or a fragment thereof, is fused to glutathione S-transferase (GST). As a consequence, the first polypeptide can be bound to a plate, e.g. to a multi-well plate suitable for HTS. The second polypeptide, which comprises the Grasp55 binding partner, is added to the plate, either with or without the candidate compound, and the plate is washed. In the absence of the candidate compound, or if the candidate compound does not inhibit the interaction between the first polypeptide and the second polypeptide, the second polypeptide binds to the first polypeptide. In contrast to this, if the candidate compound inhibits the interaction, the second polypeptide is removed upon washing. In addition, the second polypeptide is biotinylated. Therefore, upon addition of a horseradish peroxidase (HRP) bound to streptavidin, said HRP will indirectly bind to the first polypeptide only if the candidate compound is not an antagonist of Grasp55. The binding of the horseradish peroxidase (HRP) to the second polypeptide (and thus the first polypeptide) can then easily be assessed by adding a chromogenic HRP substrate. If the Optical density (OD) is lower in the presence of the candidate compound than in the absence of the candidate compound, then the candidate compound is capable of inhibiting binding of the first polypeptide to the second polypeptide (i.e. it is an antagonist of Grasp55).

Therefore, in a preferred embodiment of the screening method according to the invention, the step of determining whether the candidate compound is capable of inhibiting binding of the first polypeptide to the second polypeptide is carried out through an ELISA assay wherein:

the first polypeptide further comprises an amino acid sequence encoding glutathione S-transferase (GST); and the second polypeptide is biotinylated.

By "glutathione S-transferase" or "GST" is meant an enzyme capable of catalyzing the following reaction: RX+glutathione<=>HX+R-S-glutathione (Enzyme classification: EC 2.5.1.18). The amino acid sequence encoding GST may for example comprise or consist of the sequence of SEQ ID NO: 22.

The step of determining whether the candidate compound is capable of inhibiting binding of the first polypeptide to the second polypeptide may for example comprise:

incubating a plate (e.g. a multi-well plate such as a ninety-six-well plate) with the first polypeptide, wherein said plate is coated with glutathione;

optionally washing the plates;

optionally incubating the plates (e.g. for 2 hours) in a blocking buffer (e.g. a buffer containing PBS and 2% of bovine albumin);

adding the second polypeptide, either alone or together with the candidate compound (for example, when a multi-well plate is used, the second polypeptide is added alone in at least one well, and the second polypeptide is added together with various candidates compounds in the other wells);

washing the plates (e.g. three times);

adding a horseradish peroxidase that is bound to streptavidin;

adding a chromogenic substrate of HRP such as e.g., 3,3', 5,5'-tetramethylbenzidine (TMB), 3,3'-diaminobenzidine (DAB) or 2,2'-azino-bis(3-ethylbenzthiazoline-6-sulphonic acid) (ABTS);

measuring the optical density (OD), e.g. through measuring the absorbance at an OD of 450 nm. The absorbance may for example be measured on an ELISA POLARstar reader;

wherein the measure of an OD that is lower in the presence of the candidate compound than in the absence of the candidate compound indicates that the candidate compound is capable of inhibiting binding of the first polypeptide to the second polypeptide.

Once a candidate compound capable of inhibiting binding of the first polypeptide to the second polypeptide has been isolated, the method may further comprise the step of confirming this capacity using another assay, e.g., performing a Western-blot for JAM-C or JAM-A, performing a flow cytometry for surface expression of adhesion receptor interacting with Grasp55, and/or measuring soluble JAMs release.

Finally, the method may further comprise the step of determining or confirming, in a cellular or a non-human animal model of a disease selected from the group consisting of cell adhesion molecules implicated diseases, CD146 or JAMs implicated diseases, cancer, metastases, and inflammatory disease, whether a compound selected as described here above is capable of treating said disease. When a non-human animal model is used, said non-animal model is preferably sacrificed at the end of the experiment.

For example, the capacity of the compound to treat or to prevent cancer, in particular to prevent metastases, may for example be assessed using the B16F10 metastasis assay. Briefly, C57BL/6 mice (e.g. 15 wk old) can be injected intravenously, for example in the retroorbital vein of mice (e.g. with $1\times10^5$ cells in 100 µl), with the tumor melanoma cell line B16F10, in order to produce experimental lung metastasis. Mice are then sacrificed, e.g. after 14 days. Finally, the lungs can be flushed from blood, isolated and examined for the presence of established foci of macroscopic metastasis in the five lobes.

According to another aspect, the invention concerns an in vitro method for determining the response to a cell adhesion molecules implicated diseases therapy, a CD146 or JAMs implicated diseases therapy, an anti-inflammatory therapy or a cancer therapy in an individual, said method comprises the step of measuring the inhibition of Grasp 55 interactions with junctional adhesion molecule in a biological sample from said individual e.g., performing a Western-blot for JAM-C or JAM-A, performing a flow cytometry for surface expression of adhesion receptor interacting with Grasp55, and/or measuring soluble JAMs release.

In some embodiments, Grasp55, soluble JAM-C and/or soluble JAM-A may be used as biomarkers of the response to a JAMs implicated diseases therapy, an anti-inflammatory therapy or a cancer therapy in an individual. The term "biomarker" means a distinctive biological or biologically-derived indicator of a process, event, or condition. According to the present invention the level of expression and/or the release of the biomarker according to the invention, are/is a distinctive indicator of the response of an individual to a JAMs implicated diseases therapy, an anti-inflammatory therapy or a cancer therapy, in particular, the inhibition of Grasp55 interaction with JAMs proteins.

Pharmaceutical Compositions Comprising an Antagonist of Grasp55

The present invention also provides a pharmaceutical composition comprising an antagonist according to the invention and a pharmaceutically acceptable carrier. Pharmaceutical compositions formulated in a manner suitable for administration to human are known to the skilled in the art. The pharmaceutical composition of the invention may comprise stabilizers, buffers, and the like. The compositions of the present invention may be formulated and used as tablets, capsules or elixirs for oral administration, suppositories for rectal administration, sterile solutions or suspensions for injectable administration. The choice of the formulation ultimately depends on the intended way of administration, such as e.g. an intravenous, intraperitoneal, subcutaneous or oral way of administration, or a local administration via tumor injection. The pharmaceutical composition according to the invention may be a solution or suspension, e.g. an injectable solution or suspension. It may for example be packaged in dosage unit form.

All references cited herein, including journal articles or abstracts, published patent applications, issued patents or any other references, are entirely incorporated by reference herein, including all data, tables, figures and text presented in the cited references.

Although having distinct meanings, the terms "comprising", "having", "containing' and "consisting of" may be replaced with one another throughout the above description of the invention.

In the frame of the present description, all compounds, polypeptides and peptides may optionally be isolated and/or purified.

The invention will be further evaluated in view of the following examples and figures.

BRIEF DESCRIPTION OF THE FIGURES

FIG. 2: Characterization of interaction domains of Grasp55 and JAM-A, -B, -C proteins by yeast two-hybrid assay. Left panel: Schematic representation of constructs used for yeast two-hybrid. To confirm and extend the interaction observed using biochemistry, we developed a yeast two-hybrid method in order to map the interaction domains of Grasp55 and JAM-A, JAM-B and JAM-C. Since four GRASP55 isoforms, differing at either their C-terminus or by the presence of the first PDZ domain, have been reported; we generated several GRASP55 constructs in GAL4 two-hybrid vector system (Clontech Laboratories, Inc). Right panel: Results of yeast two-hybrids. Results from the interaction matrix using constructs depicted above are shown. A white spot indicates yeast growth and represents a positive interaction. The cytoplasmic tail of MAGUK 7 RTK was used as negative control. Constructs containing the PDZ binding motifs of JAM-A, JAM-B and JAM-C interact with wt Grasp55, but neither with Grasp55 lacking the first PDZ domain nor with the isolated first or second PDZ domains of GRASP55. This suggests that the first PDZ domain of Grasp55 is necessary, but not sufficient to support this interaction, indicating that different Grasp55 isoforms may differentially interact with the JAMs.

FIG. 9: Upper panel: Alignment of peptides used in the present study and predicted consensus sequence binding to Grasp55. The sequences binding to Grasp 55 (JAM-A, JAM-B, JAM-C) or lacking interaction (JAM-AΔ, JAM-BΔ, JAM-CΔ) are shown. The consensus sequence deduced from amino-acid properties is shown, wherein stars highlight the amino acids of the consensus sequence. All protein sequences ending with this consensus sequence are predicted to interact with Grasp55. For the alignment, the Clustal X program was used whereby:

G and A are interchangeable (small)
F and Y are interchangeable (aromatic)
S and T are interchangeable (nucleophilic)
D and E are interchangeable (acidic)
Q and N are interchangeable (amide)
K, H, R are interchangeable (basic)
V, L, I are interchangeable (hydrophobic)

Lower panel: Dark and light shading indicate identical and conserved regions, respectively, for mouse and human JAMs family members. Residues from the consensus sequence shown in the upper panel are marked by asterisks and entirely contained within conserved regions.

FIG. 10: Protein sequence alignment of mouse and human orthologs. Protein sequence of mouse and human GRASP55 are shown. Sequence comparison reveals that N-terminal PDZ domains in mouse and human GRASP55, are almost identical with a difference of one amino-acid at position 82 (A>T).

Figure 11:
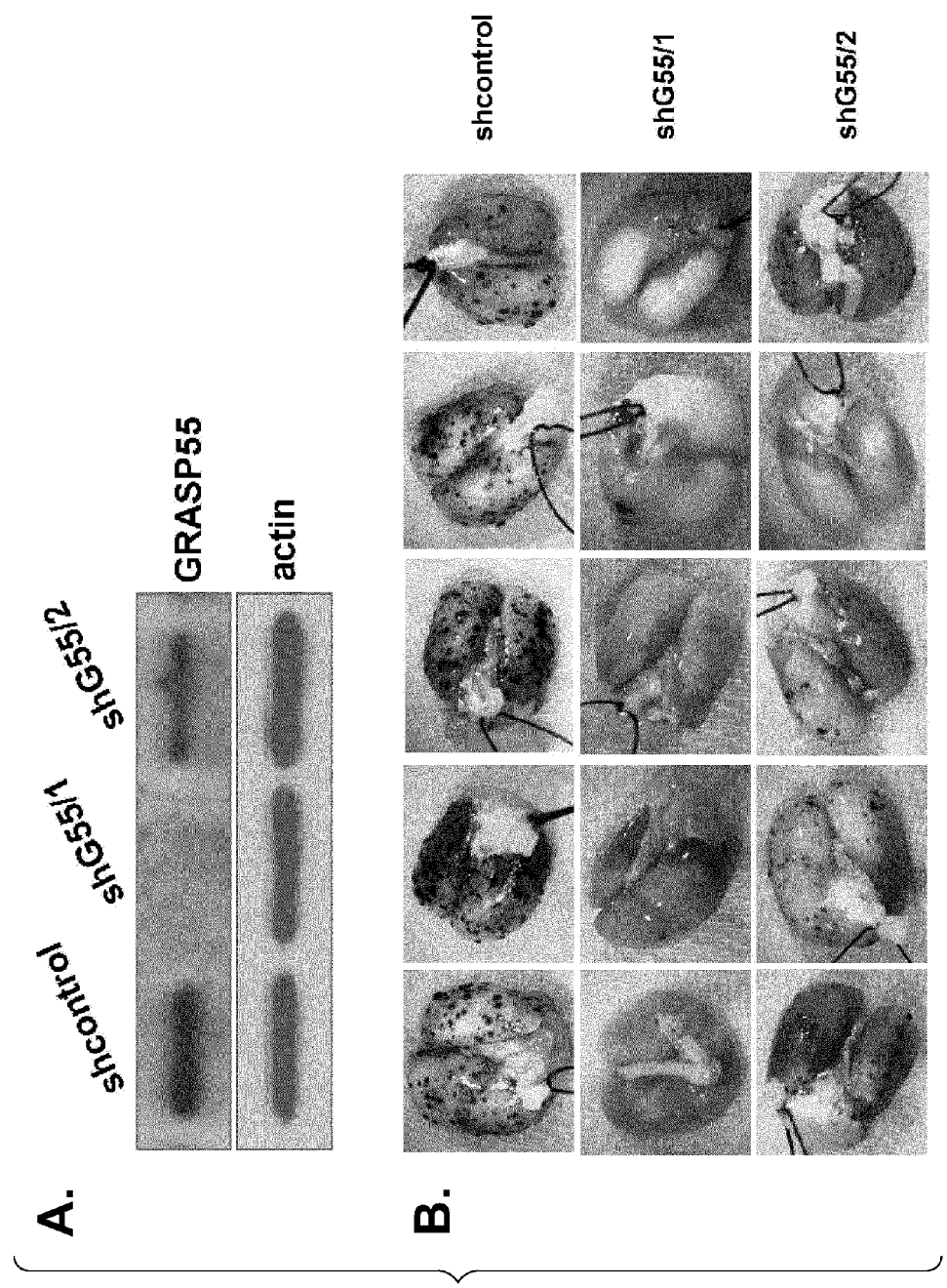

FIG. 11: Silencing of GRASP55 expression reduces development of lung metastasis. A. (Upper panel) Western blot analysis of GRASP55 expression in B16F10 melanoma cell line stably expressing shRNA control targeting luciferase (shcontrol) and two clones shRNA targeting GRASP55 expression (shG55/1 and shG55/2). Actin was used as a loading control. B. (Lower panel) Macroscopic aspect of lungs with metastasis from three groups of mice injected with clones of B16F10 expressing different level of GRASP55 protein (shcontrol, shG55/1 and shG55/2) is shown. Metastasis appear as black dots on the surface of the lungs due to the presence of melanine in B16F10, the presence of melanine in the three cell lines was checked and was not affected by silencing Grasp55 expression. The development of lung metastasis is positively correlated with the level of expression of GRASP55 protein. n=5 mice per group.

Figure 12:
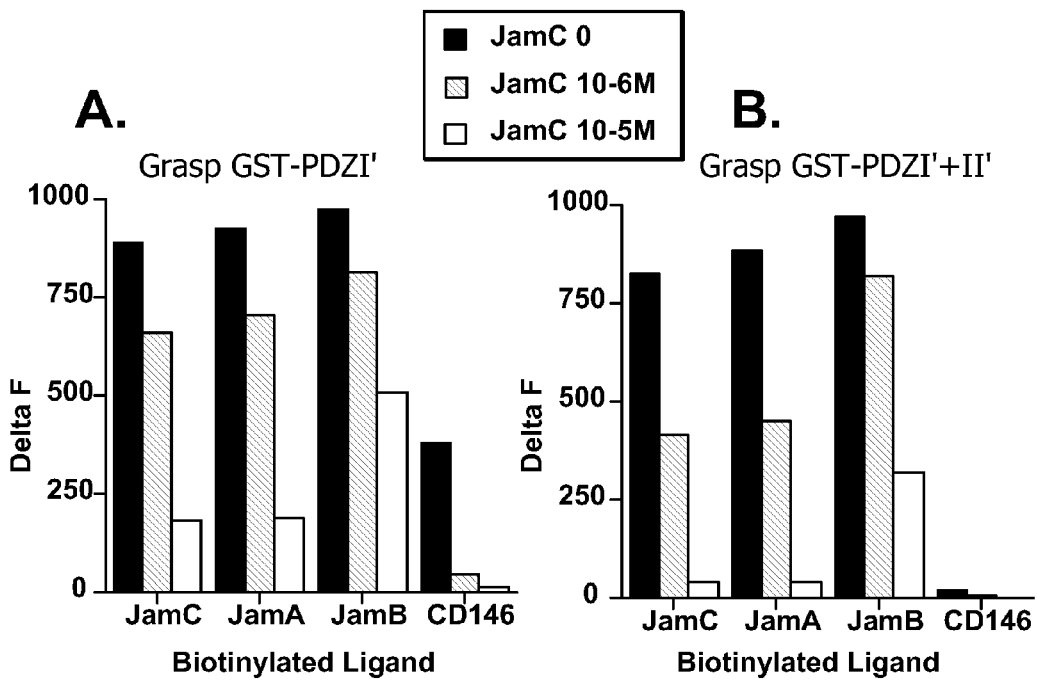

FIG. 12: (A, Left panel) Graphs show the specific binding of indicated peptides to Grasp-GST-PDZI' constructs. Signals are competed by two different concentrations of unlabelled JAM-C peptides. (B; Right panel) Graphs show the specific binding of indicated peptides to Grasp-GST-PDZI'+II' constructs. No binding could be detected with the CD146 peptide indicating that the presence of the second PDZ domain of Grasp55 in the construct restricts interaction to JAM peptides. Signals are competed by two different concentrations of unlabelled JAM-C peptides.

Figure 13:
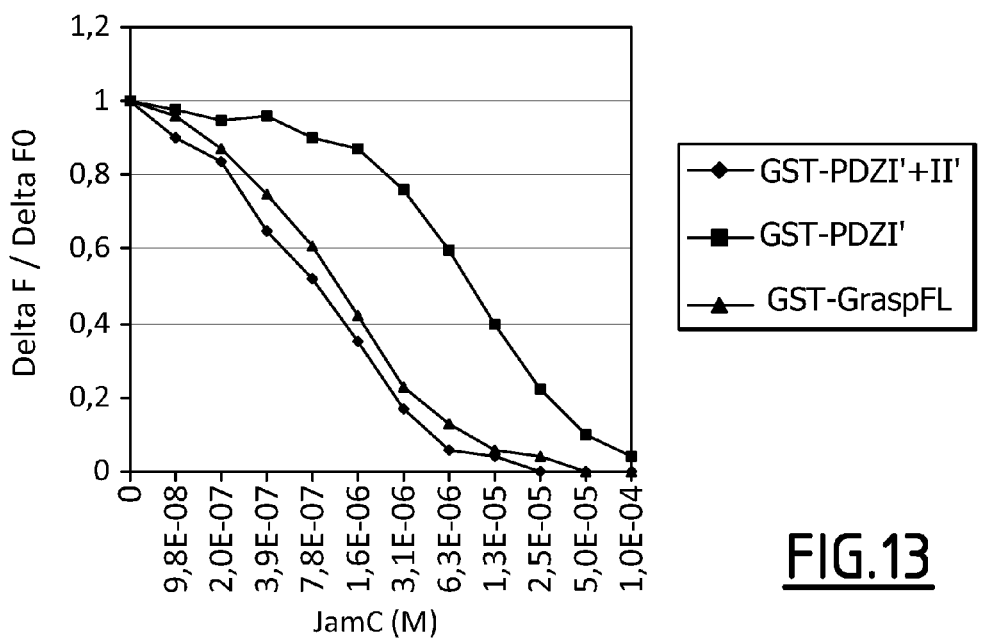

FIG. 13: The graph shows the competition curves obtained with the unlabelled JAM-C peptide at the indicated concentrations. Results are expressed as relative signals to the signals obtained in absence of competing peptide. The EC50 is in the low micromolar range for GST-PDZI'+II' and Grasp Full Length recombinant proteins.

Figure 14:
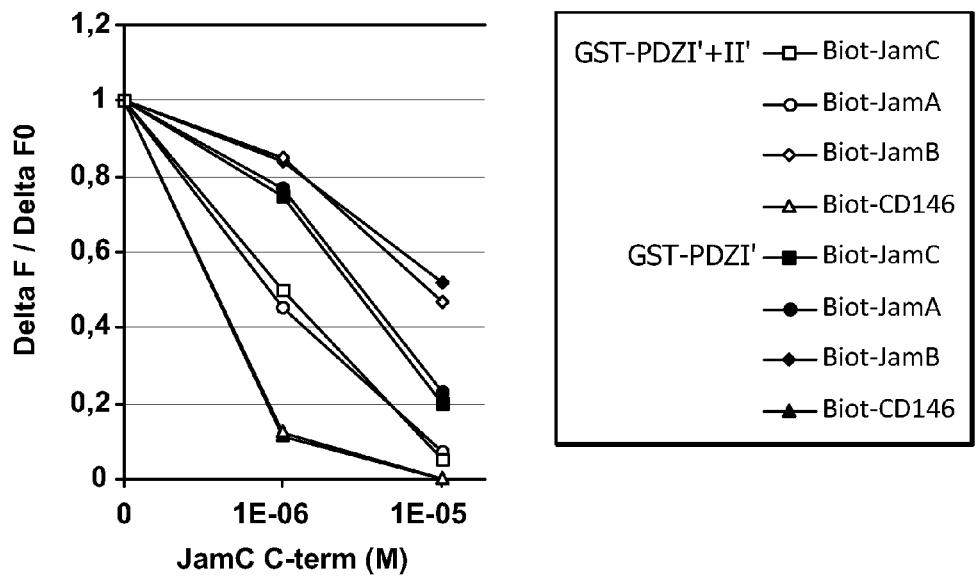

FIG. 14: The graph shows the competition of unlabelled JAM-C peptide with the indicated combinations of biotynilated peptides and GST-PDZI'+II' (empty symbols) or GST-PDZI' (black filled symbols) recombinant proteins.

Figure 15:
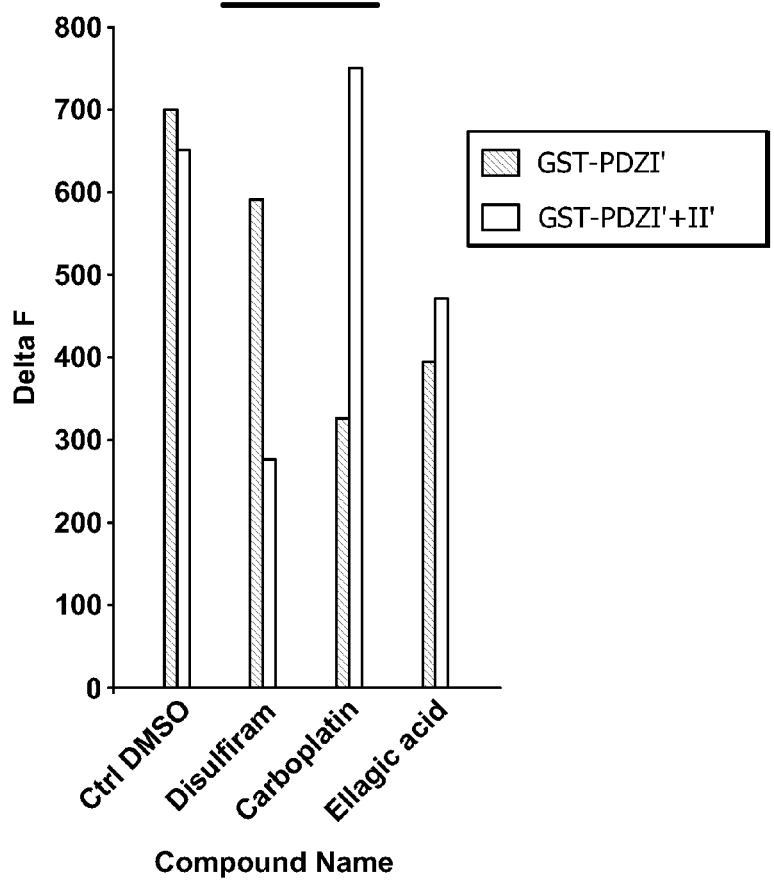

FIG. 15: Result of NINDS library screening: Twenty compounds inhibit significantly the signal as compared to the Mean value obtained with DMSO control in 104 replicates. Some of them preferentially inhibit the interaction of JAM-C with PDZI' (carboplatin), while other inhibit interaction with PDZI' and PDZI'+II' (Ellagic Acid) or only with PDZI'+II' (Disulfiram) recombinant GST proteins.

Figure 16:
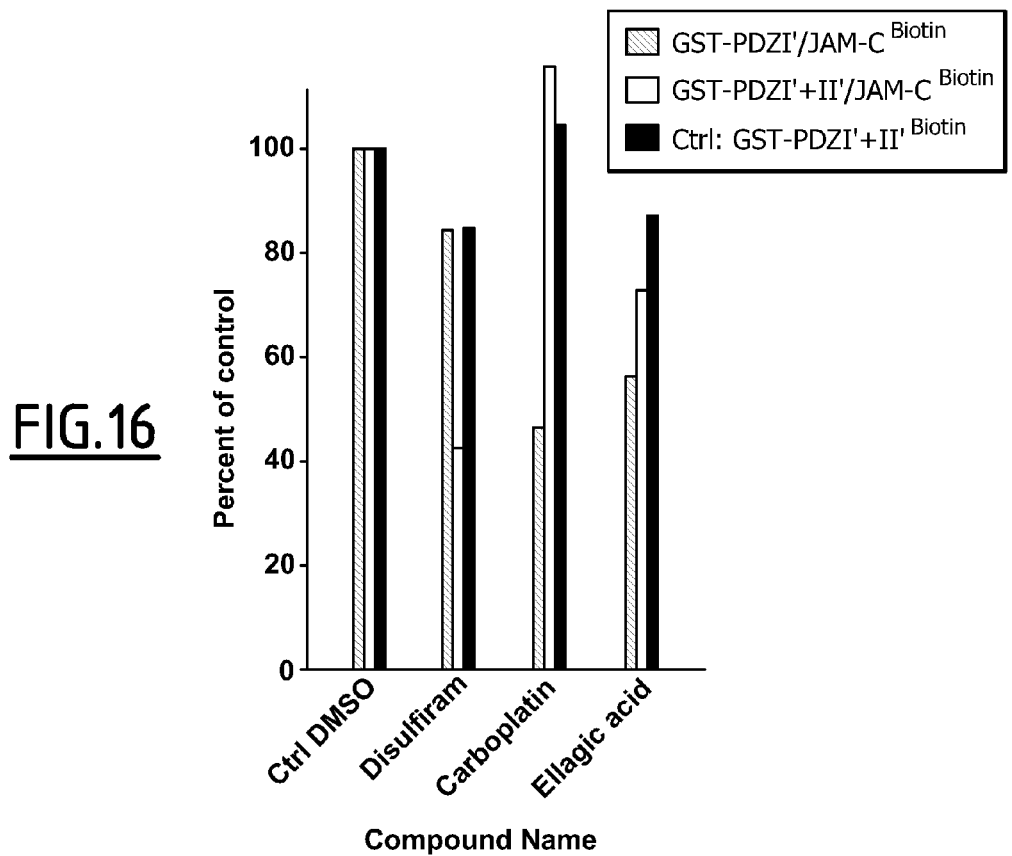

FIG. 16: Data summarize the results of the library screening expressed as percent of controls. Three compounds (Disulfiram, Carboplatin and Ellagic Acid) do not modify the signal obtained in the control condition (Black bars) but inhibit the binding of JAM-C to the GST fusion constructs (striped bars and white bars). They can be considered as real hits. Other compounds have only slight effects on the specific signals when compared to the changes observed in the control condition.

Figure 17:
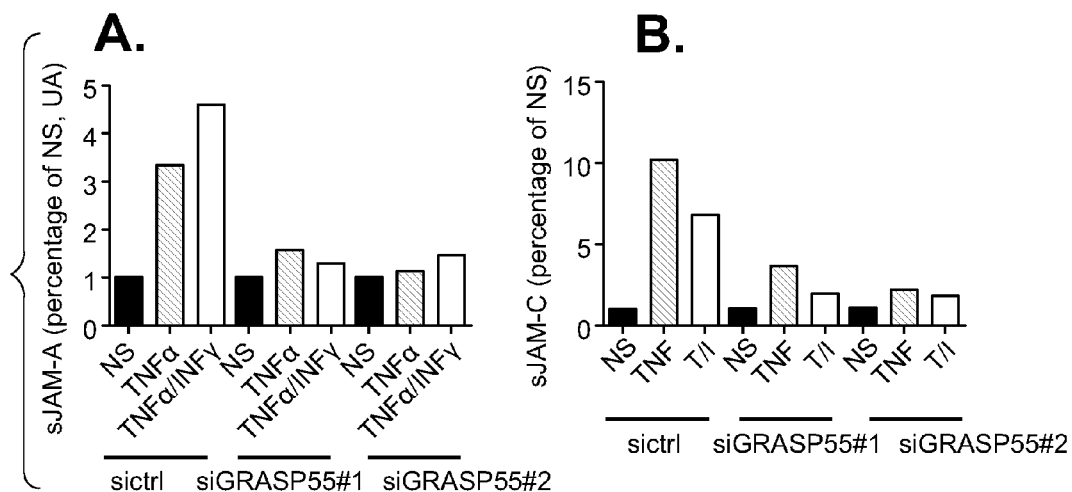

FIG. 17: (A, Left Panel) Graph showing the quantity of soluble JAM-A detected by ELISA in the supernatant of HUVECs upon 48 hours of the indicated stimulation (NS: not stimulated). (B, Right Panel) Same as left panel except that soluble JAM-C is detected. Results are expressed as fold increase over the quantity detected in the supernatant of unstimulated cells.

BRIEF DESCRIPTION OF THE SEQUENCES

SEQ ID NO: 1 shows an amino acid sequence of murine Grasp55.
SEQ ID NO: 2 shows an amino acid sequence of human Grasp55.
SEQ ID NO: 3 shows an amino acid sequence of murine JAM-A.
SEQ ID NO: 4 shows an amino acid sequence of murine JAM-B.
SEQ ID NO: 5 shows an amino acid sequence of murine JAM-C.
SEQ ID Nos. 6 to 10 show the sequences of siRNAs targeting Grasp55.
SEQ ID NO: 11 shows the sequence targeted by an shRNA targeting Grasp55.
SEQ ID Nos. 12 and 13 show the sequence of the sense and antisense strands of an shRNA targeting Grasp55.
SEQ ID Nos. 14 to 21 show the sequences of primers used in the Examples.
SEQ ID NO: 22 shows the sequence of the glutathione S-transferase used in the ELISA assay for detection of the interaction between Grasp55 and JAM-C.
SEQ ID NO: 23 shows an amino acid sequence of human JAM-A.
SEQ ID NO: 24 shows an amino acid sequence of human JAM-B.
SEQ ID NO: 25 shows an amino acid sequence of human JAM-C.
SEQ ID Nos. 26 to 40 show sequences shown on FIGS. 9 and 10.
SEQ ID NO: 41 shows the amino acid sequence of murine ADAM 10 used in yeast two hybrid assay described in Table I.

SEQ ID NO: 42 shows the amino acid sequence of murine ADAM17 used in yeast two hybrid assay described in Table I.

EXAMPLES

Example 1

Material and Methods

Plasmids, Cell Culture and Transfection

B16F10 melanoma cell line (ATCC) was grown in DMEM (Dulbecco' Minimum Essential Medium with high glucose, Invitrogen) supplemented with 10% fetal calf serum (FCS), 1% L-Glutamine, 1% penicillin and streptomycin, 1% Na-pyruvate, 1% essential amino-acids, and 25 µmol/l of β-mercaptoethanol. Primary lung mouse endothelial cells (LMEC) were isolated from mouse lungs and cultured in DMEM F12 containing 20% FCS, 1% L-Glutamine, 1% penicillin and streptomycin, 1% Na-pyruvate, 1% essential amino-acids, 25 µmol/l of β-mercaptoethanol, 100 µg/ml ECGS, 10 U/ml Heparin, 1 µg/ml hydrocortisone, 1 ng/ml bFGF and 10 ng/ml of EGF.

Plasmids containing either shRNA against luciferase or shRNA against GRASP55 and GRASP55 variants, fused with EYFP or mCherry were generated in pSUPER.retro or pEYFP-N1 or pmCherry-N1 plasmids, respectively (Clontech). shRNA against luciferase was kindly provided by Michael Sebbagh, CRCM, Marseille.

Transient transfections were performed on a 50% confluent monolayer of B16F10 cells with either 10 nM of siRNA or 5 µg of shRNA against luciferase used as a control or shRNA against GRASP55 in Lipofectamine RNAimax (Invitrogen). Transfection efficiency was monitored at 24 h by qRT-PCR and Western blots for the expression of GRASP55 transcript or protein. For selection of stable transfectants, cells were grown in DMEM containing 10 µg/ml of puromycine (Sigma Aldrich) starting 48 h after transfection.

Antibodies

Anti-mouse JAM-C and JAM-B rabbit polyclonal antibodies were obtained by immunizing rabbits with the recombinant soluble JAM-C or JAM-B proteins that contain the $V_H$-$C_2$ domains. Antibodies were produced by Covalab (Lyon, France). Rat monoclonal antibody (mAb) H36 directed against mouse JAM-C was previously described (Aurrand-Lions et al., 2001a; Aurrand-Lions et al., 2001b; Johnson-Leger et al., 2002b). Rat IgG$_{2a}$ anti-human CD44 (Hermes, 9B5) mAb used as isotype control was previously described (Lamagna et al., 2005a). Rat mAb JB4 against mouse JAM-B was obtained by immunization of rat with a recombinant JAM-B molecule containing the $V_H$-$C_2$ domains. The rat mAb H202 against mouse JAM-A has been described (Malergue). Antibody against mouse CD146 was a kind gift from Francoise Dignat-George, Faculty of Pharmacy, Marseille. The molecules GRASP55 and actin were detected with antibodies purchased from Interchim and Sigma Aldrich, respectively. Protein blots were probed with HRP-conjugated secondary antibodies (Jackson Research Laboratories) and detected with ECL reagents (Amersham). Anti-rat PE and anti-rabbit FITC, used for FACS staining were purchased from Jackson Immunoresearch Laboratories. Recombinant mouse JAM-B/Fc and JAM-C/Fc Chimeras were purchased from R&D.

Immunoprecipitation and Western Blotting

Immunoprecipitations of mouse JAM-A, B, C and CD146 were performed with rat mAb anti-JAM-C 19H36, rat anti-JAM-B JB4, rat anti-JAM-A H202 and rat anti-CD146 AMM1 and by using HNTG (50 mM Hepes pH=7.5, EGTA 1 mM, Triton 1%, Glycerol 10%, NaCl 150 mM, MgCl$_2$ 1.5 mM, NaF 0.2% and proteases inhibitors) or TNT lysis buffer (Tris 50 mM pH=7.5, EGTA 1 mM, Triton 1%, NaCl 150 mM, MgCl$_2$ 1.5 mM, NaF 0.2% and proteases inhibitors (Roche Diagnostics). After SDS-PAGE and nitrocellulose membrane transfer of the immunoprecipitates, proteins were revealed with anti-GRASP55, anti-JAM-C or anti-actin antibodies and then subsequently with anti-rabbit HRP (Jackson Immunoresearch Laboratories) and ECL detection reagents (Amersham Pharmacia Biotech). Protein concentration of the samples was determined according to the Bradford method.

Generation of GST-GRASP55 Fusion Protein and their Production

The murine wild type GRASP55 protein and its various domains were excised from the pcDNA3.1+ plasmid in which they were previously cloned. Fragments of interest excised from pcDNA3.1+ were separated by gel electrophoresis, purified and ligated with linearized pGEX4T1 containing a GST protein tag. These constructs were transformed in the bacteria Rosetta to produce the various GST-GRASP55 proteins. A pre-culture of a bacterial colony of each of plasmid construct was cultivated for 16 h under agitation at 37° C. in 3 ml of LB medium containing ampicillin. The next day, 200 ml of LB medium supplemented with ampicillin were inoculated with 500 µl of pre-culture. When the bacterial culture was in exponential growth phase (OD600 nm=0.6-0.8), the biosynthesis of the given proteins was induced by addition of Isopropyl β-D-1-thiogalactopyranoside, IPTG (0.5 mM) at 22° C. for 16 h. The bacterial culture was centrifuged at 3000×g for 30 min and bacterial pellets lysed in TNT lysis buffer (10 mM Tris-HCl, pH 7.5, 150 mM NaCl and 1% Triton) supplemented with protease inhibitors (Roche) at 4° C. The bacterial suspension is then sonicated 5 times during 10 seconds with amplitude of 30% and immediately followed by a centrifugation during 40 min at 2000×g at 4° C. These various bacterial supernatants were verified by SDS-PAGE and Coomassie blue staining for expression of the GST-GRASP55 fusion proteins.

ELISA Assay for Detection of the Interaction Between GRASP55 and JAM-C.

To set up ELISA test, various proteins of soluble GST-GRASP55 proteins were incubated on ninety-six-well plates (Nalge Nunc International) coated with glutathione. Plates were then washed and blocked with buffer containing PBS and 2% of bovine albumin for 2 hours. Biotinylated peptides corresponding to the C-terminus of JAM-C with or without the PDZ binding motif were subsequently added. After three successive washes, streptavidin-HRP was added to reveal the various complexes, followed by a HRP substrate, tetramethylbenzidine (TMB). Absorbance (OD$_{450\,nm}$) was determined on an ELISA POLARstar reader. Results were either expressed as mean of absolute relative absorbance units or percent of negative control corresponding to the signals obtained with GST alone.

Yeast Two-Hybrid System

The different GRASP55 constructs were cloned into pGBT9 GW vector (Gal4 DNA-binding domain fusion vector, Trp) as well in the pACT2 GW vector (Gal4 DNA-activation domain fusion vector, Leu) using the Gateway technology (Invitrogen). Plasmids were then co-transformed in AH109 yeast strain (/MATa, trp1-901, leu2-3, 112, ura3-52, his3-200, gal4/A, /gal80/A, /LYS2::GAL1//UAS//-GAL1//TATA//-HIS3, GAL2//UAS//-GAL2//TATA//-ADE2, URA3::MEL1//UAS//-MEL1//TATA//-lacZ, MEL1/) in accordance with the previously described transformation protocol (Chien et al. 1991. Proc Natl Acad Sci USA. 88:9578-82). Following co-transformation with the two vectors containing the different constructs (as well as the empty vector to test self activation), yeasts were plated onto Synthetic Complete (SC) medium minus Leucine (−L), minus Tryptophan (−W), minus Histidine (−H) and incubated at 30° C. for 4 to 5 days. All yeast media were prepared as previously described.

ELISA Assay for Measuring of Soluble JAM-C in Cell Culture Supernatant

An ELISA was designed to determine the concentration of soluble JAM-C in cell culture supernatants. Ninety-six-well plates (Nalge Nunc International) were coated overnight at room temperature with rat anti-mouse JAM-C antibody H36 (home-made). Plates were washed and blocked with buffer containing PBS and 2% of bovine albumin for 2 hours. Cell culture supernatants from different cell conditions were incubated during 3 hours. Plates were washed, and polyclonal rabbit anti-JAM-C (501) was added for 1 hour at room temperature. After three washes, donkey anti-rabbit HRP antibody was put on. To reveal the final read out, the substrate of HRP, tetramethylbenzidine (TBS) is adjoined. The absorbance lecture (D.O at 450 nm) is carried out on a ELISA POLARstar reader.

Wound Healing Assay

For in vitro wound healing assays, 80% confluent monolayers of wild-type B16F10 cells or B16F10 cells transfected with various siRNA or shRNA were grown in both chambers of Ibidi culture inserts with defined cell free gaps. Cells were subjected to serum starvation for 24 h, before wounds were created by removing Ibidi culture inserts that define cell gaps of 400 µm. The wound healing was carried out for 8 h in complete DMEM medium and was recorded at various times after wounding. Analysis of wound closure was performed using Metamorph software and is expressed as mean speed per minute.

qRT-PCR

Total RNA from cells was extracted using the RNeasy kit (Qiagen). cDNA was obtained from 1 µg of total RNA employing oligo(dT) and Superscript II reverse transcriptase (Invitrogen). qRT-PCR analysis using SYBR Green (Applied Biosystem) and the designed primers was carried out. 10 min of initial enzyme activation at 95° C. were followed by 40 cycles at 95° C. for 15 sec and at 60° C. for 1 min. A final 10 min extension was performed at 72° C. Oligonucleotide primers were designed for mouse JAM-C (forward: 5' tgt gag gtc gtt gct cta aat ga 3' (SEQ ID NO: 14); reverse: 5' cac tgg ctt cac ttg cac aat t 3' (SEQ ID NO: 15)), mouse Grasp55 (forward: 5' TCG GTT TGC CAG AGC TCG 3' (SEQ ID NO: 16); reverse: 5' ggg aat gac ggg agg aag tc 3' (SEQ ID NO: 17)) and mouse HPRT (forward: 5' ggccctctgtgtgctcaag 3' (SEQ ID NO: 18); reverse: 5' ctgataaaatctacagtcataggaatgga 3' (SEQ ID NO: 19)). The average cycle threshold value (CT) of HPRT measurements in a qRT-PCR experiment was used to normalize the tested genes. The average CT values were determined by carrying out at least triplicate qRT-PCR measurements for each gene in each experimental condition.

SiRNA and shRNA Against GRASP55

The sequences of siRNA used for our study are the following:

siGRASP55#01
(SEQ ID NO: 6)
(siRNA ID: s88628, 5'CGUCAUGAAUGAGUCUGAATT 3');

siGRASP55#1
(SEQ ID NO: 7)
(siRNA ID: s88629, 5'AAGUGAUCAUCACACCAAATT 3');

siGRASP55#2
(SEQ ID NO: 8)
(siRNA ID: s88630, 5' CGGUUCAAGAUUAAAUAAATT 3');

siGRASP55#3
(SEQ ID NO: 9)
(siRNA ID: J-063639-09, 5'GCAUCUCUAUUACGGUUUA 3');

siGRASP55#4
(SEQ ID NO: 10)
(siRNA ID: J-063639-10, 5' UGUAGCUACUUAACGGUAU 3');

sicontrols siGRASP55 #01, #1 and #2 were purchased from Ambion whereas sicontrols siGRASP55 #3 and #4 were from Dharmacon.

To construct the pSuper.retro.shRNAGRASP55 vector, a pair of oligonucleotides (forward and reverse oligos) containing the 19-nt RNAi target sequence derived from the mouse GRASP55 mRNA transcript was designed. The forward oligonucleotide included a BglII restriction site at the 5' end; the 21-nt RNAi target sequence (SEQ ID NO: 11) in both sense and antisense orientations separated by a 9-nt spacer sequence is designed to generate a hairpin. The reverse oligonucleotide included a HindIII restriction site at the 5' end. (Forward: 5' GATCCCCCGGTTCAAGAT-TAAATAAATTTTCAAGAGAAATTTATT-TAATCTTGAACCGT TTTTGGAAA 3' (SEQ ID NO: 20); Reverse: 5'AGCTTTTCCAAAAACGGTTCAAGAT-TAAATAAATTTCTCTTGAAAATTTATTTAATCTTG AAC CGGGG 3' (SEQ ID NO: 21)). The two oligonucleotides were then annealed and inserted into the linearized pSUPER.retro plasmid. This oligonucleotide mixture was incubated at 90° C. for 4 min then at 70° C. for 10 min, cooled slowly at 37° C. for 20 min and stored at −20° C. The annealed oligonucleotides were ligated with the linearized pSUPER-.retro plasmid and transformed into the bacteria. Bacterial clones were analyzed by restriction profile and sequenced for the presence of shRNA sequence against GRASP55.

Flow Cytometry

B16F10 cells ($1\times10^5$) were labeled with 1/1000 dilution of supernatant of either anti-JAM-C polyclonal antibody 501 (home-made), or 1 µg/ml of anti-Jam-C mAb, or isotype-matched control in cold PBS and 0.2% FCS. After wash with PBS, cells were incubated with rat anti-rabbit-FITC or donkey anti-rat-PE (Jackson Immunoresearch) and fixed for 10 min on ice in the presence of 1% paraformaldehyde. FACS analysis was conducted on FACS-Scan device.

Statistical Analysis

All data were analyzed for statistical significance using GraphPad Prism software and Student t-test.

In Vivo Experiments

C57BL/6 (15 wk old) (Charles River Laboratories, L'Arbresle, France) mice were used as immunocomptetent syngenic recipients for B16F10 metastasis assay. Tumor melanoma cell line B16F10 with high lung metastazing ability was obtained through ATCC. Cells grown in tissue culture were trypsinized, washed and resuspended in saline. They were injected intravenously, in retroorbital vein of mice ($1\times10^5$ cells in 100 µl) to produce experimental lung metastasis. Mice were sacrificed after 14 days, the lungs were flushed from blood, isolated and examined for the presence of established foci of macroscopic metastasis in the five lobes. Three groups of mice (n=5) were used for three clones of B16F10 with different expression of GRASP55 protein.

Example 2

Grasp 55 is a Binding Partner of JAMs

The inventors have developed a proteomic approach in order to identify specific protein binders of JAM-B and JAM-C cytoplasmic domains by means of peptide pull-down approaches. Immunoprecipitation of lung carcinoma cell lysates (KLN205) were performed using biotinylated peptides corresponding to the last 19 amino-acids of JAM-B and JAM-C, which cover the PDZ binding motifs present at their C-termini. As control, the same peptides, but deleted of the last three amino-acids known as the functional PDZ binding motif of JAM family members, were used.

In addition to the known ZO-1 and ZO-2 binding partners of JAM-B and JAM-C, the inventors unexpectedly found another binding partner, namely Grasp55. This protein was found by mass spectrometry, in the protein lane corresponding to the pull-down performed with JAM-B peptide, but not with the JAM-B control peptide.

Figure 1:
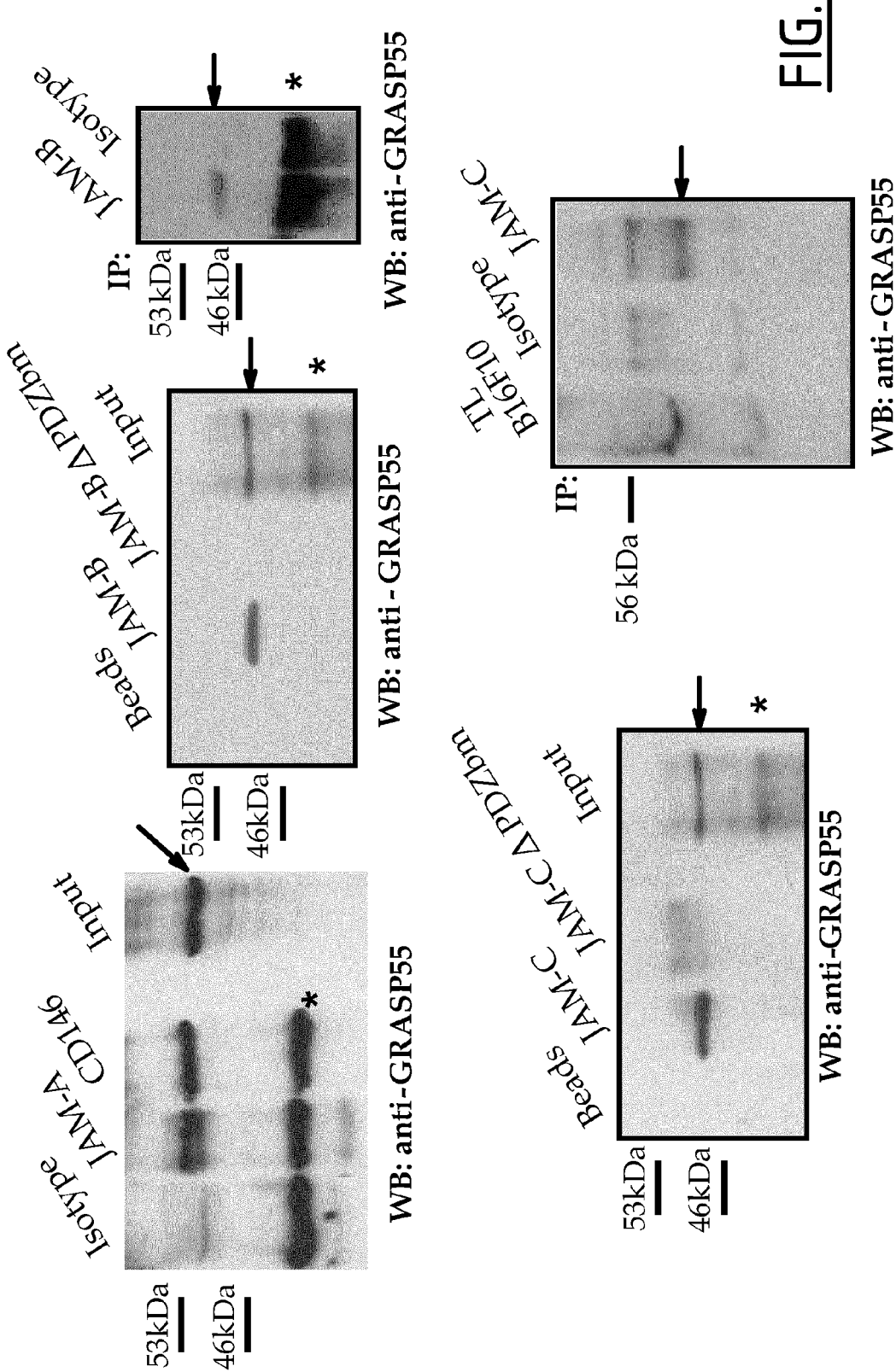
FIG. 1: JAMs members and CD146 interact with a new intracellular partner GRASP55. Endogenous interactions of JAM-A, JAM-B, JAM-C and CD146 with Grasp55 are shown by means of immunoprecipitation in B16F10 melanoma or primary lung endothelial mouse cells (LMEC). Peptide pull-down using a peptide corresponding to the last 19 amino-acids of JAM-B and JAM-C, or a peptide deleted from the last three amino-acids, are also shown. Total cell lysates were used as controls. Proteins were then resolved on SDS-PAGE and blotted with anti-GRASP55 antibody. Arrows indicate the signal corresponding to Grasp55.

To explore the physiological relevance of Grasp55 interaction with cell surface receptors, the inventors performed co-immunoprecipitation experiments using antibodies directed against JAM-A, JAM-B, JAM-C and CD146. An association between all four adhesion molecules with Grasp55 was found (FIG. 1).

To further explore whether interaction occurred directly or indirectly, JAM-B and JAM-C were used as prototypical examples, and peptide pull-down assays were performed. In this experimental set-up, the peptide sequence corresponding to the last 19 amino-acids of JAM-B and JAM-C were used to pull-down cell lysates. It was found that Grasp55 was immunoprecipitated with the peptide whereas the sequence lacking the last three amino-acids of JAM-B and JAM-C were unable to immunoprecipitate Grasp55 (FIG. 1).

These results indicate that cell surface adhesion molecules are endogenously associated with Grasp55 in tumoral and endothelial cell lines and that the interaction is mediated by direct interaction as demonstrated by peptide pull-down using either JAM-B or JAM-C.

To further refine and extend our observations, we then used yeast two-hybrid technique to identify the critical sequences necessary and sufficient to support JAM-A, JAM-B and JAM-C interaction with Grasp55. We found that deletion of the last three amino-acids of either JAM-A, -B or -C sequences abolished the interaction (FIG. 2) indicating a similar mode of protein interaction for all three family members. On the other hand, a minimum sequence encoding for the PDZ domains I and II of Grasp 55 was necessary to sustain the interaction whereas a construct containing only the first PDZ domain of Grasp55 was unable to interact. The combined results obtained by yeast two-hybrid and peptide pull-down allow to conclude that the minimal sequences necessary to get interaction between Grasp and JAM family members correspond to:

amino-acids 1 to 160 of murine Grasp 55
amino-acids 260 to 299 of murine JAM-A
amino-acids 258 to 298 of murine JAM-B
amino-acids 263 to 310 of murine JAM-C.

Example 3

Silencing Grasp55 Affects Adhesion Molecule Expression

Since Grasp55 has been previously involved in vesicular trafficking and protein transport, the inventors hypothesized that silencing Grasp55 expression may result in altered adhesion molecule expression such as JAM-C, which in turn regulate cell adhesion, cell migration, inflammation, tumor growth and angiogenesis.

Figure 3:
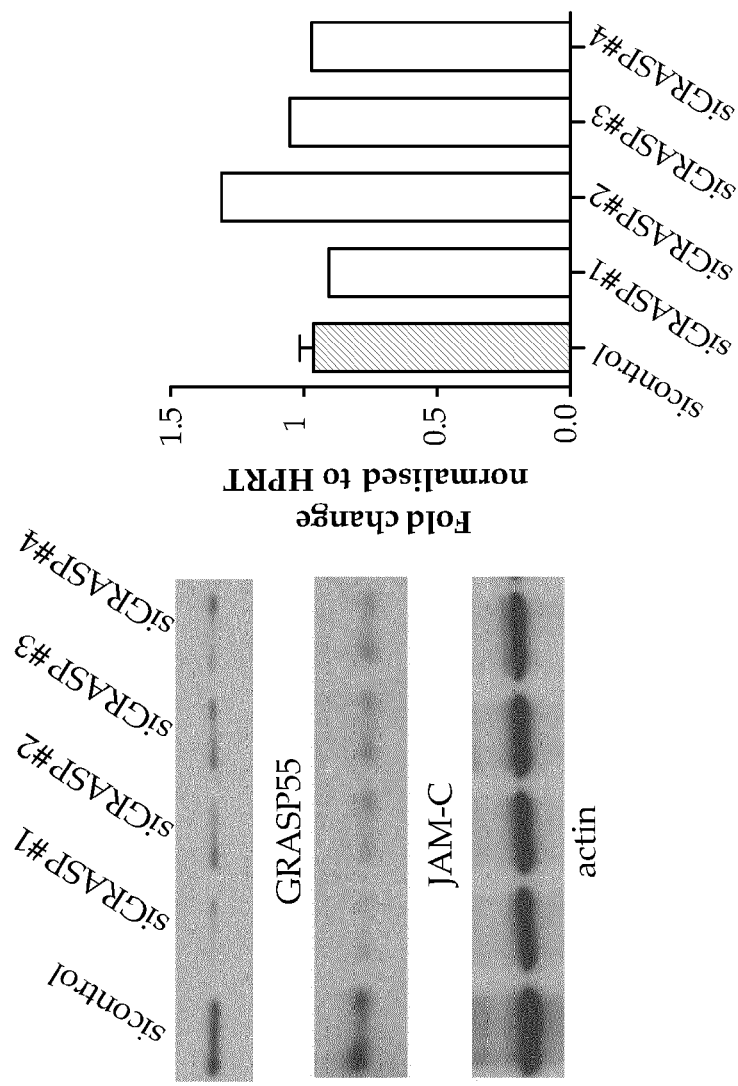
FIG. 3: Grasp55 silencing controls protein stability of JAM-C in B16F10 cells. Left panel: Inhibition of GRASP55 expression in B16F10 cells by RNAi sequence targeting was determined by RT-qPCR analysis. Transfection of GRASP55-targeted (siGRASP#1, 2, 3, 4) and siRNA control off target (sicontrol) was carried out using Lipofectamine 2000, and expression of target and internal control genes was analyzed at 12 hours post-transfection. Expression of GRASP55 is normalized to mouse HPRT and is presented as the fold change in expression relative to control off-target siRNA treated cells. (Middle panel) At 12 h post-transfection, cell lysates were analyzed for GRASP55 and JAM-C protein expression. Decrease in cell expression of GRASP55 as well as that of JAM-C in GRASP55 silenced cells was measured in comparison with control siRNA-treated cells whereas total actin expression was unaltered. Right panel: The level of Jam-C transcripts is not changed upon transfection of B16F10 cells with siRNA directed against GRASP55. Overall these results indicate that silencing of GRASP55 does not affect transcription of JAM-C but decreases protein expression levels, indicating that stability of the JAM-C protein is compromised.
Figure 4:
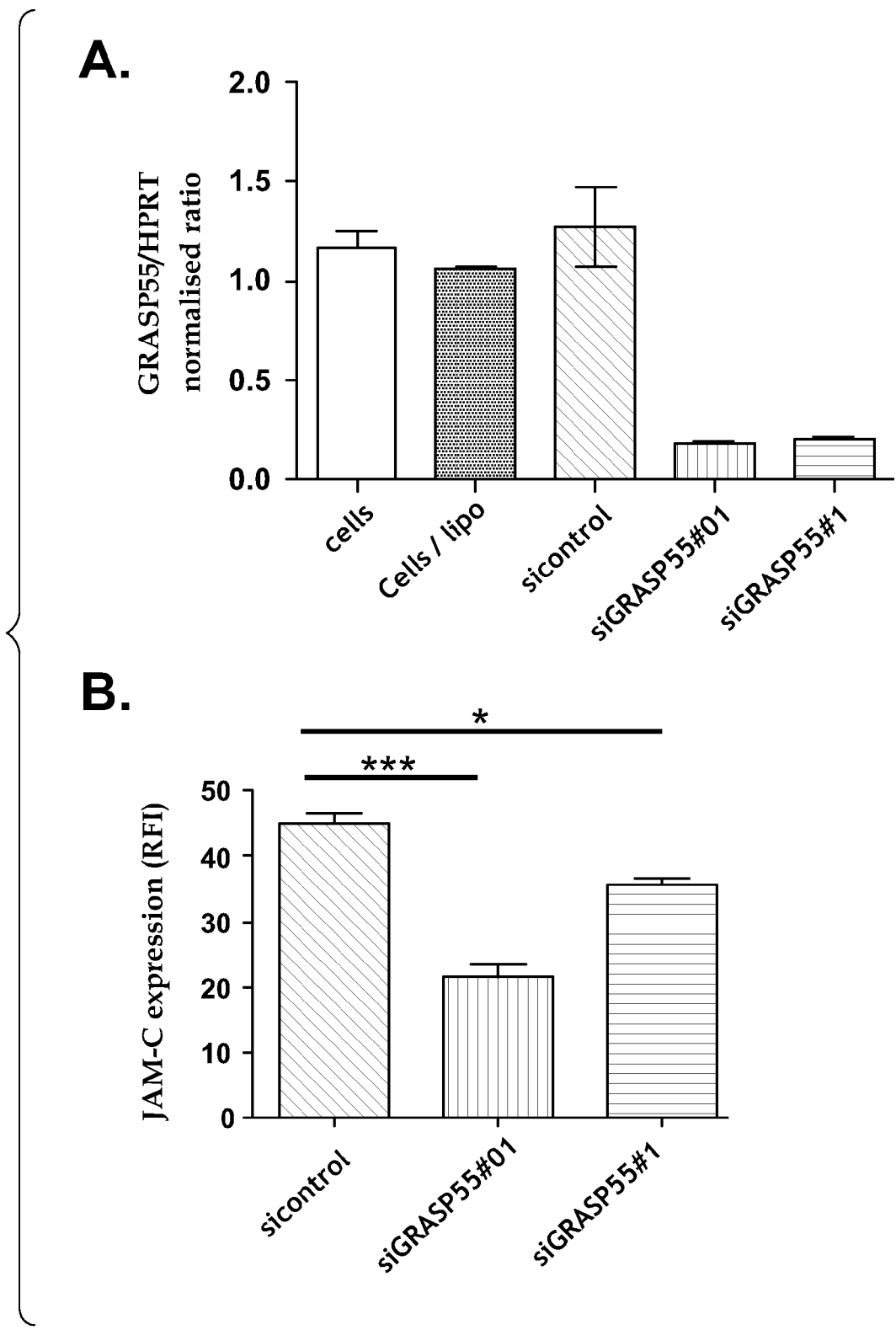
FIG. 4: Grasp55 silencing alters cell surface expression of JAM-C in B16F10 cells. Upper panel: Inhibition of GRASP55 expression in B16F10 cells by RNAi sequence targeting GRASP55 was determined by RT-qPCR analysis. Transfection of GRASP55-targeted (siGRASP#01 or siGRASP#1) and siRNA control off target (sicontrol) was carried out using Lipofectamine 2000, and .expression of target and internal control genes was analyzed at 48 hours post-transfection. Expression of GRASP55 is normalized to mouse HPRT and is presented as the fold change in expression relative to control off-target siRNA treated cells. Lower panel: Histogram showing the median relative fluorescence intensity of cell surface expression of JAM-C in siRNA GRASP55 or sicontrol targeted cells. The first histogram corresponds to isotype control for JAM-C antibody.
Figure 5:
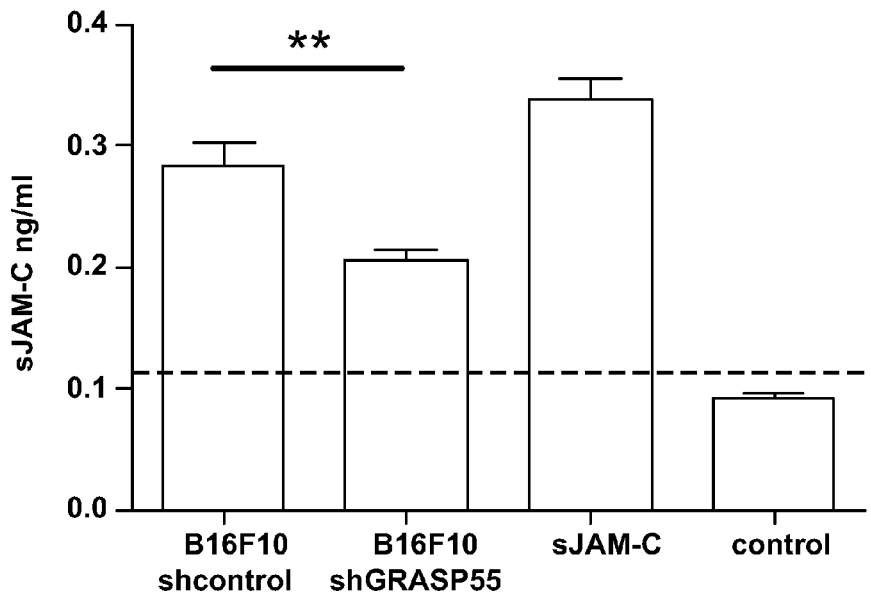
FIG. 5: Silencing of Grasp55 expression in B16F10 melanoma cells decreases the release of soluble JAM-C. The quantity of soluble JAM-C present in cell culture supernatants of B16F10 cells transfected with the indicated siRNA was measured by ELISA assays performed on concentrated culture supernatants. Results indicate that soluble JAM-C is present in supernatant of B16F10 cells (0.27±0.02 ng/ml, dark grey histogram). The quantity of soluble JAM-C is decreased in cell culture supernatants of B16F10 upon silencing of GRASP55 expression by means of shRNA (0.21±0.01 ng/ml, white histogram). As positive and negative controls, recombinant soluble mouse JAM-C (light grey histogram) and cell culture medium (black histogram) were used. Results are expressed as mean±SEM.

It was shown that silencing Grasp55 expression, by means of several siRNAs, decreased JAM-C protein stability in the B16F10 mouse melanoma cell line (FIG. 3). This was accompanied by a decrease in JAM-C cell surface expression (FIG. 4). In addition a decrease in the release of soluble JAM-C was observed in B16F10 cells silenced for Grasp55 expression by shRNA (FIG. 5).

Figure 6:
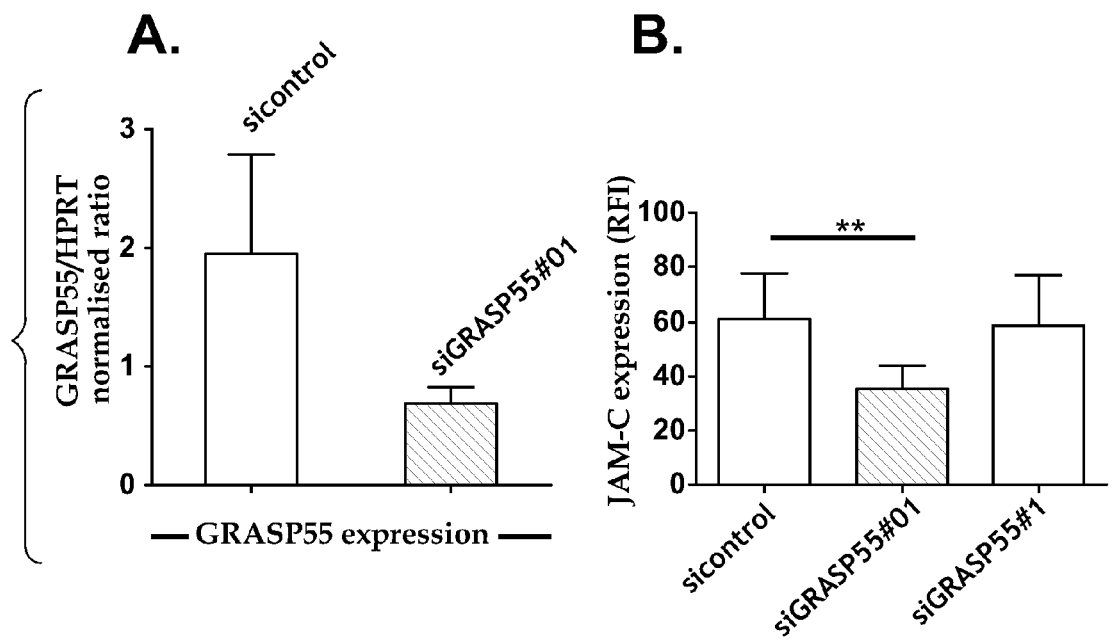
FIG. 6: GRASP55 silencing alters cell surface expression of JAM-C in LMEC cells. A (left panel): Inhibition of GRASP55 expression in primary LMEC cells by RNAi sequence targeting GRASP55 was determined by RT-qPCR analysis. Transfection of GRASP55-targeted (siGRASP#01 or siGRASP#1) and siRNA control off target (sicontrol) was carried out using Lipofectamine 2000, and expression of target and internal control genes was analyzed at 72 h hours post-transfection. Expression of GRASP55 is normalized to mouse HPRT and is presented as the fold change in expression relative to control off-target siRNA treated cells. B (right panel): The histogram shows the median relative fluorescence intensity of cell surface expression of JAM-C in siRNA GRASP55 or sicontrol targeted lung microvascular endothelial cells, LMEC. The first histogram corresponds to isotype control for JAM-C antibody. RT-qPCR, reverse transcription-quantitative polymerase chain reaction; RNAi—RNA interference.

To extend our observation to a different cellular model, similar experiments were performed in primary mouse endothelial cells (LMEC). Reduced cell surface expression of JAM-C was also observed upon Grasp55 silencing in LMECs (FIG. 6).

These data are the first demonstration that altering Grasp55 expression affects adhesion molecule expression using the prototypical member of the JAM family, JAM-C, and most likely the biological function associated to JAM-C expression.

Figure 7:
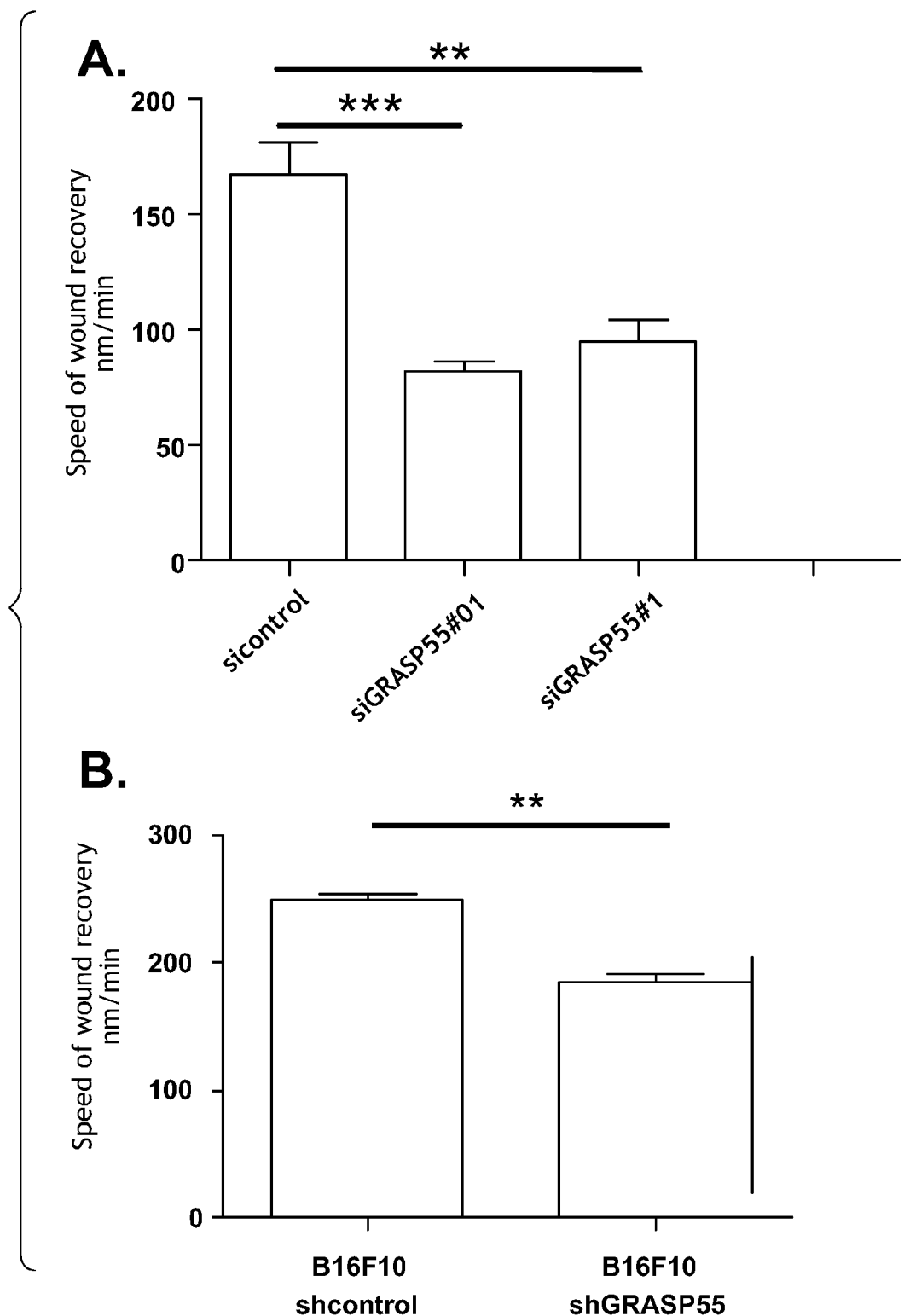
FIG. 7: Grasp55 expression controls cell migration in B16F10 cells. A. Upper panel: Cell migration was studied by wounding assays in B16F10 cells targeted with siRNA GRASP55 or siRNA control 48 h post-transfection. Histogram plots represent the mean velocity measured over 6 h by time lapse microscopy with an incubation chamber set at 37° C. and 5% $CO_2$. (sicontrol 167±13 n=33; siGRASP55#01 82±4 n=25; siGRASP55#1 95±8 nm/min n=24). B. Lower panel: Same as in the other panel, except that the experiment was performed using B16F10 cell lines stably transfected with different shRNAs (shctrl 249±5 n=34; shGRASP55 184±6 n=21). Results are expressed as Mean velocity+/−SEM, one representative experiment is shown.

To further strengthen this finding, migration assays using B16F10 cells, for which it is known that migration is correlated to JAM-C expression, were carried out. Reduced cell migration was observed when cells were lacking Grasp55 expression (due to the use of a siRNA or a shRNA) (FIG. 7). This indicates that Grasp55 directly controls cell migration and constitute a new target for therapeutic approaches aiming at impairing cell migration.

Example 4

Silencing Grasp55 Affects the Development of Lung Metastasis In Vivo

Given the finding that B16F10 melanoma cell lines silenced for the expression of GRASP55 exhibit reduced migration in wound healing assays but is not affected in their growth, it was investigated whether silencing Grasp55 affects the development of lung metastasis.

To this end, B16F10 cells known to possess high lung metastatic potential were used and silenced for Grasp55 expression by means of shRNA expression. Mice were r.o. injected with two clones of B16F10 expressing reduced levels of GRASP55 protein (shG55/1 and shG55/2) as compared to control cells. After 14 days, mice were sacrificed and lungs were isolated.

The number and the size of lung metastasis appearing as black dots was significantly reduced in the groups of mice inoculated with B16F10 cells silenced for Grasp55 expression (FIG. 11). Interestingly, a direct correlation between Grasp55 silencing and metastatic potential was observed. shG55/1 cells which lacks detectable levels of Grasp55 produced only two macroscopic metastasis in five animals, whereas shG55/2, in which residual Grasp55 expression exists, exhibited only a reduction in numbers and size of metastasis as compared to control cells.

This indicates that the ability of development of B16F10 lung metastasis is directly correlated with the expression level of GRASP55 protein in tumor cells.

Example 5

Screening Assay for Identifying Grasp55 Antagonists

To provide a method to screen for compounds targeting Grasp55 activity, an ELISA assay that allows to measure interaction between Grasp55 and its binding partners was designed.

Figure 8:
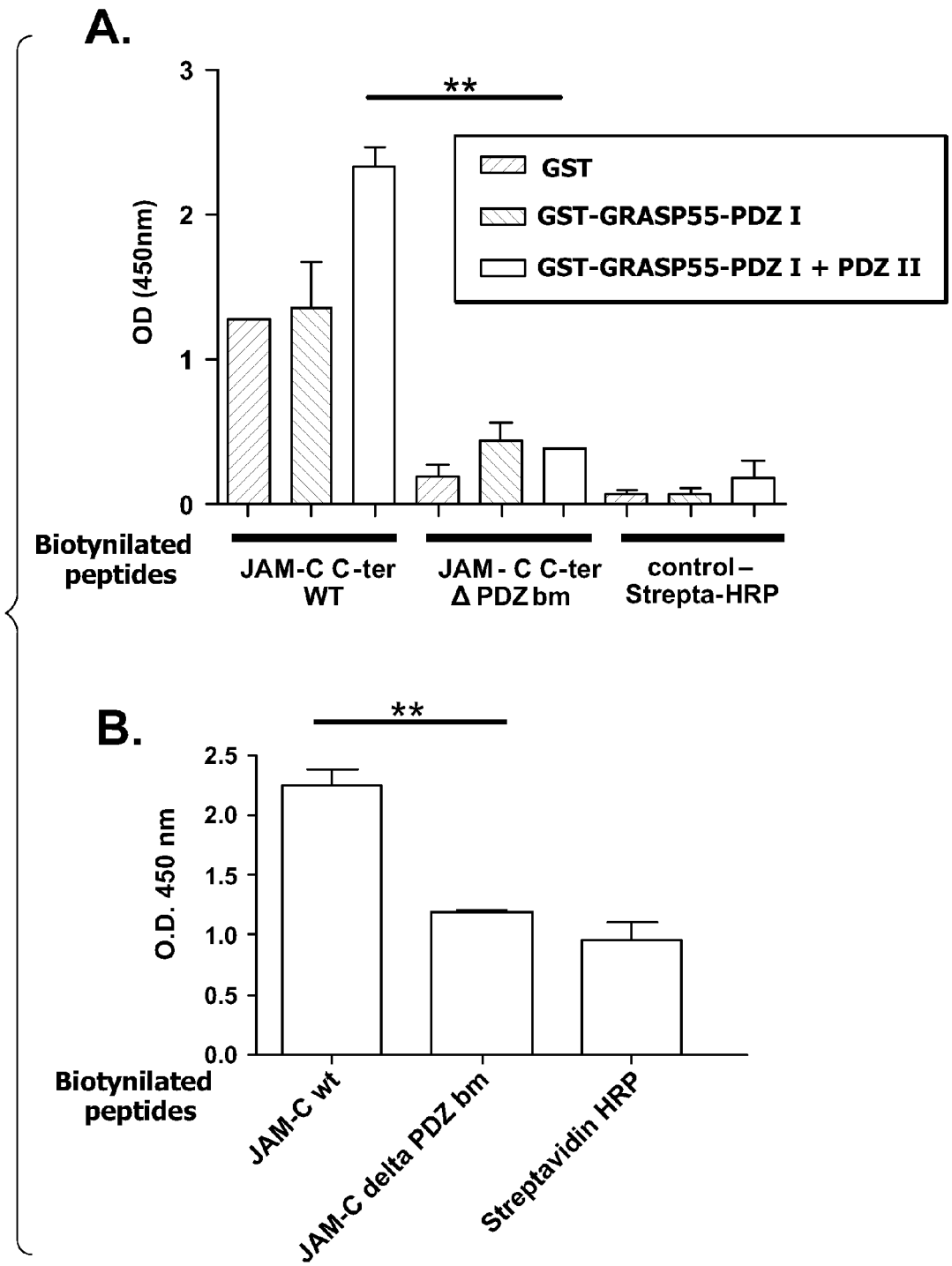
FIG. 8: ELISA assay for specific measurement of Grasp55/JAM-C interaction. (A; Upper panel): Raw results from ELISA assay using the indicated recombinant soluble molecules (GST-GRASP55 PDZ I+II, GST-GRASP55 PDZ I and GST) and JAM-C biotinylated peptides corresponding to the last 19 amino acids (aa) with or without the PDZ binding motif. Ninety-six well plates coated with glutathione were incubated overnight with various GST fusion proteins. The plates were then washed, blocked and incubated with JAMs biotinylated peptides with or without PDZ binding motif. The interaction of JAM peptides with GST-GRASP55 proteins was then revealed by adding Streptavidine-HRP and an HRP substrate. Results are expressed as Mean+/−SEM of Relative Unit of absorbance measured at 450 nm. (B; Lower panel): Same as in the other panel, but results were normalized to the negative control of each experimental condition, i.e. signals obtained on GST alone. One representative experiment is shown.

In a first approach, C-terminal peptide sequences of JAM-C and recombinant Grasp55 corresponding to the PDZ I and PDZ I+II domains were used. The C-terminal peptide sequence of JAM-C corresponding to amino acids 291-310 interacted with PDZ I+II of Grasp55, whereas deletion of either PDZII of Grasp55 or deletion of the last three amino-acids (309-310) of JAM-C abolished the interaction (FIG. 8).

The results already obtained by yeast two-hybrid (FIG. 2) indicate that peptide sequences containing the consensus sequence of the last three amino-acids in the context of conserved residues found in JAM-A, JAM-B, and JAM-C are predicted to interact with Grasp55 (FIG. 9, upper panel). These sequences are entirely contained in human orthologs (FIG. 9, lower panel), providing an assay to screen for small compounds impairing interaction between Grasp55 and cell surface adhesion molecules in humans.

Example 6

Refined Mapping of Grasp55 Interactions

In examples 2, the inventors have previously shown that interaction between Grasp55 and C-terminal part of JAM-C requires the peptidic sequence between residues 1 to 160 of Grasp55 (PDZI+II) but cannot occur with residues 1 to 79 of Grasp55 (PDZI) by yeast two hybrid and ELISA assay (FIGS. 2 and 8). In the present example, the interaction sites between JAMs or metalloproteinases involved in JAM regulation and Grasp55 have been mapped using new constructs. To this end, yeast two-hybrid and GST fusion proteins encompassing residues 1 to 107, 108 to 208, and 1 to 208 corresponding respectively to the PDZI', PDZII' and PDZI'+II' constructs have been generated. The former PDZII construct (residues 80 to 160) have also been used to test interaction with the C-terminal sequences of ADAM 10 (of sequence SEQ ID NO: 41) and ADAM 17 (of sequence SEQ ID NO: 42) known to regulate JAM-A and JAM-C release (Table 1). GST fusion proteins were produced and yeast two-hybrid assay was performed as previously described in example 1.

required for interaction with the cytoplasmic C-terminal parts of the metalloproteinases ADAM10 and 17 responsible for JAM-A and JAM-C release was mapped. A region comprising the amino-acid sequence 80 to 160 of Grasp55 was able to interact with ADAM10 and 17 indicating that the binding of JAMs and ADAMs to Grasp55 may occur simultaneously since the regions of Grasp 55 necessary for the respective interactions were only partially overlapping.

Example 7

HTRF Measurement of the Interaction of the C-Terminal JAM Peptides with Grasp55 GST-PDZ Domains To refine and extend the results obtained by yeast two hybrid, an Homogenous Time Resolved Fluorescence (HTRF) assay have been set-up to measure interactions of various peptides with recombinant GST proteins corresponding to different regions of Grasp55. The technology (Cisbio) resembles ELISA assay, but does not require washing steps and relies on proximity FRET signals between the donor that binds to the Grasp55 moiety (Anti-GST antibody) and the acceptor (Streptavidin-d2) that binds to the biotinylated peptide.

Briefly, the technique consisted in incubating 18 h at 4° C. the biotinylated-Cterminal peptides (SEQ ID NO: 26 to 34) at the concentration of $1.9*10^{-7}$M with the GST-fusion protein, the terbium-coupled anti-GST antibody ($8*10^{-10}$M each) and the d2-coupled streptavidin ($4*10^{-8}$M) (both from Cisbio), in 0.1 mL of Hepes 0.05M, NaCl 0.15M BSA 0.1% pH 7.2. In some experiments, competing peptide or chemicals were added to the incubation mix at the indicated concentration. After incubation, microtiter plates (Costar #3693) were red using PolarScan Omega (BMG Labtech) equipped for HTRF measurements. Upon excitation at 320 nm, a 620 nm fluorescence emission is produced by the donor terbium that in turn excites a 665 nm light emission by a Streptavidin-d2 (acceptor) bound to the Biotinylated interacting Peptide if the latter TABLE I present the interactions measured using yeast two hybrid technology.

| | JAM-C | JAM-C ΔPDZbm | JAM-A | JAM-A ΔPDZbm | JAM-B | JAM-B ΔPDZbm | ADAM10 | ADAM17 |
|---|---|---|---|---|---|---|---|---|
| Grasp55 FL | +++ | − | +++ | − | +++ | − | − | − |
| PDZI (1-79) | − | − | − | − | − | − | − | − |
| PDZI' (1-107) | +++ | − | NT | NT | NT | NT | − | − |
| PDZII (80-160) | − | − | − | − | − | − | +++ | +++ |
| PDZII' (108-208) | − | − | NT | NT | NT | NT | − | − |
| PDZI + II (1-160) | +++ | − | +++ | − | +++ | − | − | − |
| PDZI' + II' (1-208) | +++ | − | NT | NT | NT | NT | − | − |

Symbols "+++" and "−" indicates the growth of yeast on selective media as shown in the FIGURE 13,
NT indicates that the interaction has not been tested.

The results (Table 1) indicate that sequence 1 to 107 of Grasp55 is the minimal region of Grasp55 required for interaction with JAM-C-C-terminal region. Since the minimal consensus regions shown in example 5 (SEQ ID NO: 32, 33, 34) suggests that JAM-A and JAM-B will most likely show a pattern of interaction similar to JAM-C, they have not been tested in this assay. Finally, the minimal region of Grasp 55 is interacting with the donor. The A665/A663 R ratio is obtained and a Delta F is computed as: $[(R_{sample}-R_{NSB})/R_{NSB}]*100$ where $R_{NSB}$ is the Non Specific Background signal determined in incubates where the GST-fusion protein was omitted.

Using this technique, the interactions of JAM-A, JAM-B and JAM-C peptides with PDZI' and PDZI'+II' GST constructs have been confirmed, while CD146 interaction was only detected with PDZI'-GST-construct (FIG. 12). Consequently, the amino-acids sequence 1 to 107 of Grasp55 is minimally required for interaction with JAM-A, JAM-B, JAM-C and CD146, while the PDZ2 domain of Grasp55 in PDZII' peptide (region 108-208) restricts Grasp55 interaction to JAM family members. Control biotynilated peptide ΔPDZbm (FIG. 9, SEQ ID NO: 31) gave no signal over the background, indicating that the three terminal hydrophobic amino-acids of JAM-C are necessary for interaction with the PDZ domains of Grasp55.

In order to better define and validate this semi-High Throughput Technology for interaction measurements, a non-biotynilated peptide corresponding to JAM-C (SEQ ID NO: 30, FIG. 9) has been then used to inhibit the interaction between JAM-C and Grasp55. Results are expressed as Delta F/Delta F0 in which Delta F0 corresponds to the signal in the absence of competing peptide and provide an insight of the apparent affinity constant ($_{App}$Aff) of the binding of JAM-C to the Grasp PDZ domains. As shown in FIG. 13, the unlabelled peptide competes with the HTRF signal with EC50 in the low micromolar range for GST-PDZI'+II' and GST-GraspFL (GST-Grasp55 full length) while a twenty fold increase in EC50 is observed when GST-PDZI' construct is used. This indicates that the affinity of JAM-C interaction with Grasp55 is greatly enhanced by the presence of the PDZ2 domain of Grasp55 (PDZII' peptide) and that antagonists inhibiting Grasp55/JAM-C interaction should more preferentially be selected for their ability to interfere with GST PDZI'+II/JAM-C interaction.

Example 8

HTRF Measurement of the Interaction of the C-Terminal JAM Peptides with Grasp55 GST-PDZ Domains HTRF measurement has been further used using unlabelled JAM-C peptide to determine the relative affinity of JAM-A, JAM-B and CD146 peptides for the recombinant GST-PDZI' and GST-PDZI'+II' proteins (FIG. 14). Results indicate that the $_{App}$Aff of JAM-C is equal to $_{App}$Aff of JAM-A, higher than the $_{App}$Aff of CD146 and lower than the $_{App}$Aff of JAM-B. In addition, data indicate that JAM-B interacts equally well with recombinant GST-PDZI' and GST-PDZI'+II' proteins, while JAM-A and JAM-C displays a higher $_{App}$Aff for recombinant GST-PDZI'+II' than GST-PDZI' protein. Altogether, these results demonstrate that this assay allows identification of antagonists of Grasp55 supported interactions. The inhibition of JAM-A, CD146 and JAM-B interaction by JAM-C unlabelled peptide brings the proof of concept that natural antagonists exist and that the relative stoechiometry of Grasp55 association with JAM-A, JAM-B, JAM-C and CD146 may rely on the relative affinity of interactions with either Grasp Full Length, PDZI' polypeptide (PDZ1 domain) or PDZI'+II' polypeptide (PDZ1 and PDZ2 domains).

Example 9

NINDS Library Screening for Inhibitors of Grasp55 Interaction with JAM-C

Having shown that HTRF measurement of interaction is a reliable technology to identify inhibitors of interaction. A screen of a chemical compound library provided by MRCt has been initiated. The screening consisted in the same HTRF technique used in Example 7 except that compounds from the library were added in the incubation mix at the final concentration of $6.6 \times 10^{-5}$M. Out of 1040 compounds provided in the NINDS library, only twenty compounds reduced the Delta F signal using either the GST-PDZI' or GST-PDZI'+II' constructs and biotinylated JAM-C (FIG. 15 data shown only for Disulfiram, Carboplatin and Ellagic acid). Notably, most of the compounds inhibited the signals obtained with GST-PDZI' and GST-PDZI'+II' recombinant Grasp55 constructs. Since such a result could be either due to a specific inhibition of the JAM-C peptide interaction to the recombinant Grasp55 PDZ domains or to a non-specific inhibition of the FRET signal between donor and acceptor in HTRF technology, the twenty selected compounds have been further tested. Indeed, compounds could potentially interfere with the binding of the anti-GST antibody terbium-labeled to the GST of the fusion protein, the binding of Streptavidin-d2 to the biotinylated peptide or promote strong interference at 320, 630 or 665 nm. Thus, the putative hits obtained were screened for non-specific inhibition. To this end, the GST-PDZI'+II' recombinant protein was biotinylated using Sulfo-NHS Biotin according to manufacturer instructions (Pierce). This allows designing an HTRF assay in which the d2-coupled streptavidin (acceptor) and the terbium-coupled anti-GST antibody are directly bound to recombinant GST-PDZI'+II' protein and produce DeltaF signal independently of the biotinylated peptide. The twenty selected compounds were thus tested in this assay to eliminate those giving false inhibition of the HTRF signals while inhibitors of Biotinylated peptide interaction with GST-PDZI'+II' should not interfere in this assay.

Results show that only twelve compounds did not significantly reduce the control signals below 80% of the control signal, among which, only Disulfiram (1,1',1",1'''-[disulfanediylbis(carbonothioylnitrilo)]tetraethane), Carboplatin (cis-Diammine(1,1-cyclobutanedicarboxylato)platinum(II)) and Ellagic acid (2,3,7,8-Tetrahydroxy-chromeno[5,4,3-cde] chromene-5,10-dione) reduced the signals obtained with GST-PDZI' or GST-PDZI'+II' and biotinylated JAM-C peptide for more than 40% (FIG. 16, Black bars). Consequently, these three compounds are new antagonists of JAM-C/Grasp55 interaction and may be used as antagonist of Grasp 55 partners interacting with PDZ domains and notably PDZI' peptide for Carboplatin, PDZI'+II' peptide for Disulfiram and both peptides for Ellagic Acid.

Example 10

Grasp55 Controls JAM-A and JAM-C Responses to Inflammatory Stimulation

Numerous studies have shown that expression and release of adhesion molecules by endothelial cells are regulated by inflammation. In the case of JAM-A and JAM-C, it has been shown that disintigrin metalloproteinases ADAM10 and ADAM17 are responsible for the regulated release of soluble molecules upon TNF-α or TNF-α/IFN-γ stimulation of endothelial cells (Koenen, Blood 2009; Rabquer B J, Journal Immunol, 2010; Hou and Rabquer Ann Rheu Dis, 2010). Having shown that Grasp55 interacts with JAM-A, JAM-C, ADAM10 and ADAM17 C-terminal cytoplasmic domains (see Table 1), the inhibition effects of Grasp55 expression on JAM-A and JAM-C release upon TNF-α or TNF-α/IFN-γ stimulation of endothelial cells have been tested.
Cells, Transfection and Antibodies.

The HUVEC cells (Human Umbilical Vein Endothelial Cells) are cultivated on support covered with gelatine 0.1% in a medium for endothelial cells (PromoCell) complemented by fetal calf serum (2%), epidermal growth factor (5 ng/ml), fibroblastic growth factor (10 ng/ml), "insulin like" growth factor (20 ng/ml), vascular growth factor (0.5 ng/ml), ascorbic acid (1 µg/ml), heparin (22.5 µg/ml) and hydrocortisone (0.2 µg/ml). The HUVEC cells ($1 \times 10^6$) are transfected by the system Amaxa (Amaxa Old Nucleofactor kit, Lonza) with two siRNA directed against human GORASP2 (Silencer Select siARN, Ambion); s24914 (5'CUAUUACACCUCUUAAAGAtt3'; SEQ ID NO: 43); s24915 (5'GAGUCUGACUGGACUUUCUtt3'; SEQ ID NO: 44) and siRNA control (Thermo Scientific Dharmacon). Anti-human antibodies JAM-A and JAM-C, isotypic control and human recombinant soluble JAM-A and JAM-C proteins were provided by R&D systems. Monoclonal mouse anti-human GRASP55 (Abnova), polyclonal rabbit anti-human JAM-C (R&D), polyclonal rabbit anti-human JAM-C (home made), monoclonal mouse anti-human JAM-A (home made) and goat anti-human Jam-A (R&D) antibodies were used.

ELISA Assay.

In order to study the release of soluble forms of JAM-A and JAM-C, the HUVECs cells were stimulated with pro-inflammatory cytokines. Four hours before stimulation, the medium is replaced by medium without serum then HUVECs are stimulated by TNFα (200 ng/ml) or TNFα and Interferon-γ (200 ng/ml+200 U/ml). The supernatants of the cellular cultures are collected after twenty-four hours of stimulation then centrifuged at 11000 g. The concentration of soluble JAM-A and JAM-C in the supernatants is determined by ELISA assay. ELISA plates (96 well plates, MaxiSorp, Nunc) are incubated overnight at 4° C. with 3 µg/ml of anti-JAM-A or anti-JAM-C antibody diluted in PBS 1x, pH 7.2. They are washed five times with PBS 1x/0.05% Tween, then saturated during two hours with PBS 1x/2% BSA and incubated during two hours with the supernatants and standard curves solutions of recombinant soluble JAM-A and JAM-C proteins (1 µg/ml to 0.01 pg/ml) at 4° C. The plates are then washed and incubated with anti-human antibodies JAM-A and JAM-C (PBS 1x/0.5% BSA) during one hour at room temperature. After washing, the antibodies anti-goat HRP and anti-rabbit HRP diluted in PBS 1x/0.5% BSA are added during one hour at room temperature. At the end of the assay, the plates are washed then incubated with Tetramethylbenzidine (R&D systems). The enzymatic reaction is stopped with 2M H2SO4. The optical density is measured at 450 nm with POLARstar OMEGA (BMG LABTECH).

Results

Using two different siRNA against Grasp55 in Human Umbilical Vein Endothelial Cells (HUVECs), the release of soluble JAM-A and JAM-C upon TNF-α or TNF-α/IFN-γ stimulation has been found to be abolished (FIG. 17). This is likely due to the disassembly of a protein complex containing Grasp55, ADAM10, ADAM17 and the adhesion molecules interacting with Grasp55 that have been identified. These results indicate that JAM-A and JAM-C can be used for determining whether a compound is capable of inhibiting Grasp55 by measuring the level of release of soluble JAM-A and JAM-C.

The invention claimed is:

1. A method for treating a patient suffering from a JAM-A or JAM-C implicated disease said method comprising the step of administering an effective amount of an antagonist of the Golgi reassembly-stacking protein of 55 kDa (Grasp55) to an individual in need thereof.

2. The method of claim 1, wherein said JAM-A or JAM-C implicated disease is selected from the group consisting of cancer and an inflammatory disease.

3. The method of claim 2, wherein said cancer is metastasis.

4. The method of claim 1, wherein said antagonist is capable of reducing the amount of Grasp55 in cells.

5. The method of claim 4, wherein said antagonist is a nucleic acid targeting an mRNA encoding Grasp55.

6. The method of claim 5, wherein said nucleic acid is a siRNA or a shRNA.

* * * * *

SEQUENCE LISTING

```
<160> NUMBER OF SEQ ID NOS: 44

<210> SEQ ID NO 1
<211> LENGTH: 451
<212> TYPE: PRT
<213> ORGANISM: Mus musculus

<400> SEQUENCE: 1

Met Gly Ser Ser Gln Ser Val Glu Ile Pro Gly Gly Gly Thr Glu Gly
1               5                   10                  15

Tyr His Val Leu Arg Val Gln Glu Asn Ser Pro Gly His Arg Ala Gly
            20                  25                  30

Leu Glu Pro Phe Phe Asp Phe Ile Val Ser Ile Asn Gly Ser Arg Leu
        35                  40                  45

Asn Lys Asp Asn Asp Thr Leu Lys Asp Leu Leu Lys Ala Asn Val Glu
    50                  55                  60

Lys Pro Val Lys Met Leu Ile Tyr Ser Ser Lys Thr Leu Glu Leu Arg
65                  70                  75                  80

Glu Ala Ser Val Thr Pro Ser Asn Leu Trp Gly Gly Gln Gly Leu Leu
                85                  90                  95

Gly Val Ser Ile Arg Phe Cys Ser Phe Asp Gly Ala Asn Glu Asn Val
            100                 105                 110

Trp His Val Leu Glu Val Glu Ser Asn Ser Pro Ala Ala Leu Ala Gly
        115                 120                 125

Leu Arg Pro His Ser Asp Tyr Ile Ile Gly Ala Asp Thr Val Met Asn
    130                 135                 140

Glu Ser Glu Asp Leu Phe Ser Leu Ile Glu Thr His Glu Ala Lys Pro
145                 150                 155                 160

Leu Lys Leu Tyr Val Tyr Asn Thr Asp Thr Asp Asn Cys Arg Glu Val
                165                 170                 175
```

```
Ile Ile Thr Pro Asn Ser Ala Trp Gly Glu Gly Ser Leu Gly Cys
                180                 185                 190

Gly Ile Gly Tyr Gly Tyr Leu His Arg Ile Pro Thr Arg Pro Phe Glu
            195                 200                 205

Glu Gly Lys Lys Ile Ser Leu Pro Gly Gln Met Thr Gly Thr Pro Ile
        210                 215                 220

Thr Pro Leu Lys Asp Gly Phe Thr Glu Val Gln Leu Ser Ser Val Ser
225                 230                 235                 240

Pro Pro Ser Leu Ser Pro Pro Gly Thr Thr Gly Val Glu Gln Ser Leu
                245                 250                 255

Ser Gly Leu Ser Ile Ser Ser Ala Pro Pro Ala Val Ser Asn Val Leu
            260                 265                 270

Ser Thr Gly Val Pro Thr Val Pro Leu Leu Pro Pro Gln Val Asn Gln
        275                 280                 285

Ser Leu Ala Ser Met Pro Pro Met Asn Pro Ala Thr Thr Leu Pro Ser
    290                 295                 300

Leu Met Pro Leu Ser Ala Gly Leu Pro Ser Leu Pro Asn Leu Pro Ser
305                 310                 315                 320

Leu Ser Asn Phe Asn Leu Pro Ala Pro His Ile Met Pro Gly Val Gly
                325                 330                 335

Leu Pro Glu Leu Gly Ser Pro Gly Leu Pro Leu Pro Ser Leu Pro
            340                 345                 350

Pro Arg Asn Leu Pro Gly Ile Ala Pro Leu Pro Met Leu Ser Asp Phe
        355                 360                 365

Leu Pro Ser Phe Pro Leu Val Pro Glu Gly Ser Ser Ala Ala Ser Ala
370                 375                 380

Gly Glu Pro Leu Ser Ser Leu Pro Ala Met Gly Pro Pro Ser Asp Pro
385                 390                 395                 400

Val Met Thr Thr Ala Lys Ala Asp Ala Ser Ser Leu Thr Val Asp Val
                405                 410                 415

Thr Ser Pro Ala Ser Lys Val Pro Thr Thr Val Glu Asp Arg Val Ser
            420                 425                 430

Asp Cys Thr Pro Ala Val Glu Lys Pro Val Ser Asp Ala Asp Ala Ser
        435                 440                 445

Glu Pro Ser
    450

<210> SEQ ID NO 2
<211> LENGTH: 452
<212> TYPE: PRT
<213> ORGANISM: Homo sapiens

<400> SEQUENCE: 2

Met Gly Ser Ser Gln Ser Val Glu Ile Pro Gly Gly Gly Thr Glu Gly
1               5                   10                  15

Tyr His Val Leu Arg Val Gln Glu Asn Ser Pro Gly His Arg Ala Gly
                20                  25                  30

Leu Glu Pro Phe Phe Asp Phe Ile Val Ser Ile Asn Gly Ser Arg Leu
            35                  40                  45

Asn Lys Asp Asn Asp Thr Leu Lys Asp Leu Leu Lys Ala Asn Val Glu
        50                  55                  60

Lys Pro Val Lys Met Leu Ile Tyr Ser Ser Lys Thr Leu Glu Leu Arg
65                  70                  75                  80
```

Glu Thr Ser Val Thr Pro Ser Asn Leu Trp Gly Gly Gln Gly Leu Leu
                 85                  90                  95

Gly Val Ser Ile Arg Phe Cys Ser Phe Asp Gly Ala Asn Glu Asn Val
            100                 105                 110

Trp His Val Leu Glu Val Glu Ser Asn Ser Pro Ala Ala Leu Ala Gly
        115                 120                 125

Leu Arg Pro His Ser Asp Tyr Ile Ile Gly Ala Asp Thr Val Met Asn
    130                 135                 140

Glu Ser Glu Asp Leu Phe Ser Leu Ile Glu Thr His Glu Ala Lys Pro
145                 150                 155                 160

Leu Lys Leu Tyr Val Tyr Asn Thr Asp Thr Asp Asn Cys Arg Glu Val
                165                 170                 175

Ile Ile Thr Pro Asn Ser Ala Trp Gly Gly Glu Gly Ser Leu Gly Cys
            180                 185                 190

Gly Ile Gly Tyr Gly Tyr Leu His Arg Ile Pro Thr Arg Pro Phe Glu
        195                 200                 205

Glu Gly Lys Lys Ile Ser Leu Pro Gly Gln Met Ala Gly Thr Pro Ile
    210                 215                 220

Thr Pro Leu Lys Asp Gly Phe Thr Glu Val Gln Leu Ser Ser Val Asn
225                 230                 235                 240

Pro Pro Ser Leu Ser Pro Pro Gly Thr Thr Gly Ile Glu Gln Ser Leu
                245                 250                 255

Thr Gly Leu Ser Ile Ser Ser Thr Pro Pro Ala Val Ser Val Leu
            260                 265                 270

Ser Thr Gly Val Pro Thr Val Pro Leu Leu Pro Pro Gln Val Asn Gln
        275                 280                 285

Ser Leu Thr Ser Val Pro Pro Met Asn Pro Ala Thr Thr Leu Pro Gly
    290                 295                 300

Leu Met Pro Leu Pro Ala Gly Leu Pro Asn Leu Pro Asn Leu Asn Leu
305                 310                 315                 320

Asn Leu Pro Ala Pro His Ile Met Pro Gly Val Gly Leu Pro Glu Leu
                325                 330                 335

Val Asn Pro Gly Leu Pro Pro Leu Pro Ser Met Pro Pro Arg Asn Leu
            340                 345                 350

Pro Gly Ile Ala Pro Leu Pro Leu Pro Ser Glu Phe Leu Pro Ser Phe
        355                 360                 365

Pro Leu Val Pro Glu Ser Ser Ala Ala Ser Gly Glu Leu Leu
    370                 375                 380

Ser Ser Leu Pro Pro Thr Ser Asn Ala Pro Ser Asp Pro Ala Thr Thr
385                 390                 395                 400

Thr Ala Lys Ala Asp Ala Ala Ser Ser Leu Thr Val Asp Val Thr Pro
                405                 410                 415

Pro Thr Ala Lys Ala Pro Thr Val Glu Asp Arg Val Gly Asp Ser
            420                 425                 430

Thr Pro Val Ser Glu Lys Pro Val Ser Ala Ala Val Asp Ala Asn Ala
        435                 440                 445

Ser Glu Ser Pro
    450

<210> SEQ ID NO 3
<211> LENGTH: 300
<212> TYPE: PRT
<213> ORGANISM: Mus musculus

```
<400> SEQUENCE: 3

Met Gly Thr Glu Gly Lys Ala Gly Arg Lys Leu Leu Phe Leu Phe Thr
1               5                   10                  15

Ser Met Ile Leu Gly Ser Leu Val Gln Gly Lys Gly Ser Val Tyr Thr
            20                  25                  30

Ala Gln Ser Asp Val Gln Val Pro Glu Asn Glu Ser Ile Lys Leu Thr
        35                  40                  45

Cys Thr Tyr Ser Gly Phe Ser Ser Pro Arg Val Glu Trp Lys Phe Val
    50                  55                  60

Gln Gly Ser Thr Thr Ala Leu Val Cys Tyr Asn Ser Gln Ile Thr Ala
65                  70                  75                  80

Pro Tyr Ala Asp Arg Val Thr Phe Ser Ser Gly Ile Thr Phe Ser
                85                  90                  95

Ser Val Thr Arg Lys Asp Asn Gly Glu Tyr Thr Cys Met Val Ser Glu
            100                 105                 110

Glu Gly Gly Gln Asn Tyr Gly Glu Val Ser Ile His Leu Thr Val Leu
            115                 120                 125

Val Pro Pro Ser Lys Pro Thr Ile Ser Val Pro Ser Ser Val Thr Ile
        130                 135                 140

Gly Asn Arg Ala Val Leu Thr Cys Ser Glu His Asp Gly Ser Pro Pro
145                 150                 155                 160

Ser Glu Tyr Ser Trp Phe Lys Asp Gly Ile Ser Met Leu Thr Ala Asp
                165                 170                 175

Ala Lys Lys Thr Arg Ala Phe Met Asn Ser Ser Phe Thr Ile Asp Pro
            180                 185                 190

Lys Ser Gly Asp Leu Ile Phe Asp Pro Val Thr Ala Phe Asp Ser Gly
        195                 200                 205

Glu Tyr Tyr Cys Gln Ala Gln Asn Gly Tyr Gly Thr Ala Met Arg Ser
    210                 215                 220

Glu Ala Ala His Met Asp Ala Val Glu Leu Asn Val Gly Gly Ile Val
225                 230                 235                 240

Ala Ala Val Leu Val Thr Leu Ile Leu Leu Gly Leu Leu Ile Phe Gly
                245                 250                 255

Val Trp Phe Ala Tyr Ser Arg Gly Tyr Phe Glu Thr Thr Lys Lys Gly
            260                 265                 270

Thr Ala Pro Gly Lys Lys Val Ile Tyr Ser Gln Pro Ser Thr Arg Ser
        275                 280                 285

Glu Gly Glu Phe Lys Gln Thr Ser Ser Phe Leu Val
    290                 295                 300

<210> SEQ ID NO 4
<211> LENGTH: 298
<212> TYPE: PRT
<213> ORGANISM: Mus musculus

<400> SEQUENCE: 4

Met Ala Arg Ser Pro Gln Gly Leu Leu Met Leu Leu Leu Leu His Tyr
1               5                   10                  15

Leu Ile Val Ala Leu Asp Tyr His Lys Ala Asn Gly Phe Ser Ala Ser
            20                  25                  30

Lys Asp His Arg Gln Glu Val Thr Val Ile Glu Phe Gln Glu Ala Ile
        35                  40                  45

Leu Ala Cys Lys Thr Pro Lys Lys Thr Thr Ser Ser Arg Leu Glu Trp
    50                  55                  60
```

```
Lys Lys Val Gly Gln Gly Val Ser Leu Val Tyr Gln Gln Ala Leu
 65                  70                  75                  80

Gln Gly Asp Phe Lys Asp Arg Ala Glu Met Ile Asp Phe Asn Ile Arg
                 85                  90                  95

Ile Lys Asn Val Thr Arg Ser Asp Ala Gly Glu Tyr Arg Cys Glu Val
            100                 105                 110

Ser Ala Pro Thr Glu Gln Gly Gln Asn Leu Gln Glu Asp Lys Val Met
        115                 120                 125

Leu Glu Val Leu Val Ala Pro Ala Val Pro Ala Cys Glu Val Pro Thr
    130                 135                 140

Ser Val Met Thr Gly Ser Val Val Glu Leu Arg Cys Gln Asp Lys Glu
145                 150                 155                 160

Gly Asn Pro Ala Pro Glu Tyr Ile Trp Phe Lys Asp Gly Thr Ser Leu
                165                 170                 175

Leu Gly Asn Pro Lys Gly Gly Thr His Asn Asn Ser Ser Tyr Thr Met
            180                 185                 190

Asn Thr Lys Ser Gly Ile Leu Gln Phe Asn Met Ile Ser Lys Met Asp
        195                 200                 205

Ser Gly Glu Tyr Tyr Cys Glu Ala Arg Asn Ser Val Gly His Arg Arg
    210                 215                 220

Cys Pro Gly Lys Arg Met Gln Val Asp Val Leu Asn Ile Ser Gly Ile
225                 230                 235                 240

Ile Ala Thr Val Val Val Ala Phe Val Ile Ser Val Cys Gly Leu
                245                 250                 255

Gly Thr Cys Tyr Ala Gln Arg Lys Gly Tyr Phe Ser Lys Glu Thr Ser
            260                 265                 270

Phe Gln Lys Gly Ser Pro Ala Ser Lys Val Thr Met Ser Glu Asn
        275                 280                 285

Asp Phe Lys His Thr Lys Ser Phe Ile Ile
        290                 295

<210> SEQ ID NO 5
<211> LENGTH: 310
<212> TYPE: PRT
<213> ORGANISM: Mus musculus

<400> SEQUENCE: 5

Met Ala Leu Ser Arg Arg Leu Arg Leu Arg Leu Tyr Ala Arg Leu Pro
 1               5                  10                  15

Asp Phe Phe Leu Leu Leu Leu Phe Arg Gly Cys Met Ile Glu Ala Val
                 20                  25                  30

Asn Leu Lys Ser Ser Asn Arg Asn Pro Val Val His Glu Phe Glu Ser
            35                  40                  45

Val Glu Leu Ser Cys Ile Ile Thr Asp Ser Gln Thr Ser Asp Pro Arg
        50                  55                  60

Ile Glu Trp Lys Lys Ile Gln Asp Gly Gln Thr Thr Tyr Val Tyr Phe
 65                  70                  75                  80

Asp Asn Lys Ile Gln Gly Asp Leu Ala Gly Arg Thr Asp Val Phe Gly
                 85                  90                  95

Lys Thr Ser Leu Arg Ile Trp Asn Val Thr Arg Ser Asp Ser Ala Ile
            100                 105                 110

Tyr Arg Cys Glu Val Val Ala Leu Asn Asp Arg Lys Glu Val Asp Glu
        115                 120                 125

Ile Thr Ile Glu Leu Ile Val Gln Val Lys Pro Val Thr Pro Val Cys
    130                 135                 140
```

```
Arg Ile Pro Ala Ala Val Pro Val Gly Lys Thr Ala Thr Leu Gln Cys
145                 150                 155                 160

Gln Glu Ser Glu Gly Tyr Pro Arg Pro His Tyr Ser Trp Tyr Arg Asn
                165                 170                 175

Asp Val Pro Leu Pro Thr Asp Ser Arg Ala Asn Pro Arg Phe Gln Asn
                180                 185                 190

Ser Ser Phe His Val Asn Ser Glu Thr Gly Thr Leu Val Phe Asn Ala
                195                 200                 205

Val His Lys Asp Asp Ser Gly Gln Tyr Tyr Cys Ile Ala Ser Asn Asp
        210                 215                 220

Ala Gly Ala Ala Arg Cys Glu Gly Gln Asp Met Glu Val Tyr Asp Leu
225                 230                 235                 240

Asn Ile Ala Gly Ile Ile Gly Gly Val Leu Val Leu Ile Val Leu
                245                 250                 255

Ala Val Ile Thr Met Gly Ile Cys Cys Ala Tyr Arg Arg Gly Cys Phe
                260                 265                 270

Ile Ser Ser Lys Gln Asp Gly Glu Ser Tyr Lys Ser Pro Gly Lys His
                275                 280                 285

Asp Gly Val Asn Tyr Ile Arg Thr Ser Glu Glu Gly Asp Phe Arg His
        290                 295                 300

Lys Ser Ser Phe Val Ile
305             310

<210> SEQ ID NO 6
<211> LENGTH: 21
<212> TYPE: DNA
<213> ORGANISM: Artificial
<220> FEATURE:
<223> OTHER INFORMATION: Synthetic siRNA

<400> SEQUENCE: 6
cgucaugaau gagucugaat t                                              21

<210> SEQ ID NO 7
<211> LENGTH: 21
<212> TYPE: DNA
<213> ORGANISM: Artificial
<220> FEATURE:
<223> OTHER INFORMATION: Synthetic siRNA

<400> SEQUENCE: 7
aagugaucau cacaccaaat t                                              21

<210> SEQ ID NO 8
<211> LENGTH: 21
<212> TYPE: DNA
<213> ORGANISM: Artificial
<220> FEATURE:
<223> OTHER INFORMATION: Synthetic siRNA

<400> SEQUENCE: 8
cgguucaaga uuaaauaaat t                                              21

<210> SEQ ID NO 9
<211> LENGTH: 19
<212> TYPE: DNA
<213> ORGANISM: Artificial
<220> FEATURE:
<223> OTHER INFORMATION: Synthetic siRNA
```

```
<400> SEQUENCE: 9
gcaucucuau uacgguuua                                          19

<210> SEQ ID NO 10
<211> LENGTH: 19
<212> TYPE: DNA
<213> ORGANISM: Artificial
<220> FEATURE:
<223> OTHER INFORMATION: Synthetic siRNA

<400> SEQUENCE: 10
uguagcuacu uaacgguau                                          19

<210> SEQ ID NO 11
<211> LENGTH: 21
<212> TYPE: DNA
<213> ORGANISM: Mus musculus

<400> SEQUENCE: 11
cggttcaaga ttaaataaat t                                       21

<210> SEQ ID NO 12
<211> LENGTH: 21
<212> TYPE: DNA
<213> ORGANISM: Artificial
<220> FEATURE:
<223> OTHER INFORMATION: Synthetic shRNA (sense strand)

<400> SEQUENCE: 12
cgguucaaga uuaaauaaat t                                       21

<210> SEQ ID NO 13
<211> LENGTH: 21
<212> TYPE: DNA
<213> ORGANISM: Artificial
<220> FEATURE:
<223> OTHER INFORMATION: Synthetic shRNA (antisense strand)

<400> SEQUENCE: 13
aatttattta atcttgaacc g                                       21

<210> SEQ ID NO 14
<211> LENGTH: 23
<212> TYPE: DNA
<213> ORGANISM: Artificial
<220> FEATURE:
<223> OTHER INFORMATION: Synthetic primer

<400> SEQUENCE: 14
tgtgaggtcg ttgctctaaa tga                                     23

<210> SEQ ID NO 15
<211> LENGTH: 22
<212> TYPE: DNA
<213> ORGANISM: Artificial
<220> FEATURE:
<223> OTHER INFORMATION: Synthetic primer

<400> SEQUENCE: 15
cactggcttc acttgcacaa tt                                      22

<210> SEQ ID NO 16
<211> LENGTH: 18
<212> TYPE: DNA
<213> ORGANISM: Artificial
```

```
<220> FEATURE:
<223> OTHER INFORMATION: Synthetic primer

<400> SEQUENCE: 16
tcggtttgcc agagctcg                                                    18

<210> SEQ ID NO 17
<211> LENGTH: 20
<212> TYPE: DNA
<213> ORGANISM: Artificial
<220> FEATURE:
<223> OTHER INFORMATION: Synthetic primer

<400> SEQUENCE: 17
gggaatgacg ggaggaagtc                                                  20

<210> SEQ ID NO 18
<211> LENGTH: 19
<212> TYPE: DNA
<213> ORGANISM: Artificial
<220> FEATURE:
<223> OTHER INFORMATION: Synthetic primer

<400> SEQUENCE: 18
ggccctctgt gtgctcaag                                                   19

<210> SEQ ID NO 19
<211> LENGTH: 29
<212> TYPE: DNA
<213> ORGANISM: Artificial
<220> FEATURE:
<223> OTHER INFORMATION: Synthetic primer

<400> SEQUENCE: 19
ctgataaaat ctacagtcat aggaatgga                                        29

<210> SEQ ID NO 20
<211> LENGTH: 68
<212> TYPE: DNA
<213> ORGANISM: Artificial
<220> FEATURE:
<223> OTHER INFORMATION: Synthetic primer

<400> SEQUENCE: 20 gatccccgg ttcaagatta aataaatttt caagagaaat ttatttaatc ttgaaccgtt       60
tttggaaa                                                               68

<210> SEQ ID NO 21
<211> LENGTH: 68
<212> TYPE: DNA
<213> ORGANISM: Artificial
<220> FEATURE:
<223> OTHER INFORMATION: Synthetic primer

<400> SEQUENCE: 21
agcttttcca aaaacggttc aagattaaat aaatttctct tgaaaattta tttaatcttg      60
aaccgggg                                                               68

<210> SEQ ID NO 22
<211> LENGTH: 218
<212> TYPE: PRT
<213> ORGANISM: Schistosoma japonicum
```

```
<400> SEQUENCE: 22

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys
    210                 215

<210> SEQ ID NO 23
<211> LENGTH: 299
<212> TYPE: PRT
<213> ORGANISM: Homo sapiens

<400> SEQUENCE: 23

Met Gly Thr Lys Ala Gln Val Glu Arg Lys Leu Leu Cys Leu Phe Ile
1               5                   10                  15

Leu Ala Ile Leu Leu Cys Ser Leu Ala Leu Gly Ser Val Thr Val His
            20                  25                  30

Ser Ser Glu Pro Glu Val Arg Ile Pro Glu Asn Asn Pro Val Lys Leu
        35                  40                  45

Ser Cys Ala Tyr Ser Gly Phe Ser Ser Pro Arg Val Glu Trp Lys Phe
    50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
            100                 105                 110

Glu Glu Gly Gly Asn Ser Tyr Gly Glu Val Lys Val Lys Leu Ile Val
        115                 120                 125

Leu Val Pro Pro Ser Lys Pro Thr Val Asn Ile Pro Ser Ser Ala Thr
    130                 135                 140
```

```
Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
            165                 170                 175

Pro Lys Ser Thr Arg Ala Phe Ser Asn Ser Ser Tyr Val Leu Asn Pro
        180                 185                 190

Thr Thr Gly Glu Leu Val Phe Asp Pro Leu Ser Ala Ser Asp Thr Gly
    195                 200                 205

Glu Tyr Ser Cys Glu Ala Arg Asn Gly Tyr Gly Thr Pro Met Thr Ser
210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
                260                 265                 270

Thr Ser Ser Lys Lys Val Ile Tyr Ser Gln Pro Ser Ala Arg Ser Glu
                275                 280                 285

Gly Glu Phe Lys Gln Thr Ser Ser Phe Leu Val
    290                 295

<210> SEQ ID NO 24
<211> LENGTH: 298
<212> TYPE: PRT
<213> ORGANISM: Homo sapiens

<400> SEQUENCE: 24

Met Ala Arg Arg Ser Arg His Arg Leu Leu Leu Leu Leu Leu Arg Tyr
1               5                   10                  15

Leu Val Val Ala Leu Gly Tyr His Lys Ala Tyr Gly Phe Ser Ala Pro
            20                  25                  30

Lys Asp Gln Gln Val Val Thr Ala Val Glu Tyr Gln Glu Ala Ile Leu
        35                  40                  45

Ala Cys Lys Thr Pro Lys Lys Thr Val Ser Ser Arg Leu Glu Trp Lys
    50                  55                  60

Lys Leu Gly Arg Ser Val Ser Phe Val Tyr Tyr Gln Gln Thr Leu Gln
65                  70                  75                  80

Gly Asp Phe Lys Asn Arg Ala Glu Met Ile Asp Phe Asn Ile Arg Ile
                85                  90                  95

Lys Asn Val Thr Arg Ser Asp Ala Gly Lys Tyr Arg Cys Glu Val Ser
            100                 105                 110

Ala Pro Ser Glu Gln Gly Gln Asn Leu Glu Glu Asp Thr Val Thr Leu
        115                 120                 125

Glu Val Leu Val Ala Pro Ala Val Pro Ser Cys Glu Val Pro Ser Ser
    130                 135                 140

Ala Leu Ser Gly Thr Val Val Glu Leu Arg Cys Gln Asp Lys Glu Gly
145                 150                 155                 160

Asn Pro Ala Pro Glu Tyr Thr Trp Phe Lys Asp Gly Ile Arg Leu Leu
                165                 170                 175

Glu Asn Pro Arg Leu Gly Ser Gln Ser Thr Asn Ser Ser Tyr Thr Met
            180                 185                 190

Asn Thr Lys Thr Gly Thr Leu Gln Phe Asn Thr Val Ser Lys Leu Asp
        195                 200                 205

Thr Gly Glu Tyr Ser Cys Glu Ala Arg Asn Ser Val Gly Tyr Arg Arg
    210                 215                 220
```

Cys Pro Gly Lys Arg Met Gln Val Asp Asp Leu Asn Ile Ser Gly Ile
225                 230                 235                 240

Ile Ala Ala Val Val Val Ala Leu Val Ile Ser Val Cys Gly Leu
            245                 250                 255

Gly Val Cys Tyr Ala Gln Arg Lys Gly Tyr Phe Ser Lys Glu Thr Ser
        260                 265                 270

Phe Gln Lys Ser Asn Ser Ser Lys Ala Thr Thr Met Ser Glu Asn
    275                 280                 285

Asp Phe Lys His Thr Lys Ser Phe Ile Ile
    290                 295

<210> SEQ ID NO 25
<211> LENGTH: 310
<212> TYPE: PRT
<213> ORGANISM: Homo sapiens

<400> SEQUENCE: 25

Met Ala Leu Arg Arg Pro Pro Arg Leu Arg Leu Cys Ala Arg Leu Pro
1               5                   10                  15

Asp Phe Phe Leu Leu Leu Leu Phe Arg Gly Cys Leu Ile Gly Ala Val
            20                  25                  30

Asn Leu Lys Ser Ser Asn Arg Thr Pro Val Val Gln Glu Phe Glu Ser
        35                  40                  45

Val Glu Leu Ser Cys Ile Ile Thr Asp Ser Gln Thr Ser Asp Pro Arg
    50                  55                  60

Ile Glu Trp Lys Lys Ile Gln Asp Glu Gln Thr Thr Tyr Val Phe Phe
65                  70                  75                  80

Asp Asn Lys Ile Gln Gly Asp Leu Ala Gly Arg Ala Glu Ile Leu Gly
                85                  90                  95

Lys Thr Ser Leu Lys Ile Trp Asn Val Thr Arg Arg Asp Ser Ala Leu
            100                 105                 110

Tyr Arg Cys Glu Val Val Ala Arg Asn Asp Arg Lys Glu Ile Asp Glu
        115                 120                 125

Ile Val Ile Glu Leu Thr Val Gln Val Lys Pro Val Thr Pro Val Cys
    130                 135                 140

Arg Val Pro Lys Ala Val Pro Val Gly Lys Met Ala Thr Leu His Cys
145                 150                 155                 160

Gln Glu Ser Glu Gly His Pro Arg Pro His Tyr Ser Trp Tyr Arg Asn
                165                 170                 175

Asp Val Pro Leu Pro Thr Asp Ser Arg Ala Asn Pro Arg Phe Arg Asn
            180                 185                 190

Ser Ser Phe His Leu Asn Ser Glu Thr Gly Thr Leu Val Phe Thr Ala
        195                 200                 205

Val His Lys Asp Asp Ser Gly Gln Tyr Tyr Cys Ile Ala Ser Asn Asp
    210                 215                 220

Ala Gly Ser Ala Arg Cys Glu Glu Gln Glu Met Glu Val Tyr Asp Leu
225                 230                 235                 240

Asn Ile Gly Gly Ile Ile Gly Gly Val Leu Val Val Leu Ala Val Leu
                245                 250                 255

Ala Leu Ile Thr Leu Gly Ile Cys Cys Ala Tyr Arg Arg Gly Tyr Phe
            260                 265                 270

Ile Asn Asn Lys Gln Asp Gly Glu Ser Tyr Lys Asn Pro Gly Lys Pro
        275                 280                 285

```
Asp Gly Val Asn Tyr Ile Arg Thr Asp Glu Glu Gly Asp Phe Arg His
    290                 295                 300

Lys Ser Ser Phe Val Ile
305                 310

<210> SEQ ID NO 26
<211> LENGTH: 19
<212> TYPE: PRT
<213> ORGANISM: Artificial
<220> FEATURE:
<223> OTHER INFORMATION: Synthetic peptide

<400> SEQUENCE: 26

Ser Gln Pro Ser Thr Arg Ser Glu Gly Glu Phe Lys Gln Thr Ser Ser
1               5                   10                  15

Phe Leu Val

<210> SEQ ID NO 27
<211> LENGTH: 16
<212> TYPE: PRT
<213> ORGANISM: Artificial
<220> FEATURE:
<223> OTHER INFORMATION: Synthetic peptide

<400> SEQUENCE: 27

Ser Gln Pro Ser Thr Arg Ser Glu Gly Glu Phe Lys Gln Thr Ser Ser
1               5                   10                  15

<210> SEQ ID NO 28
<211> LENGTH: 19
<212> TYPE: PRT
<213> ORGANISM: Artificial
<220> FEATURE:
<223> OTHER INFORMATION: Synthetic peptide

<400> SEQUENCE: 28

Ser Lys Val Thr Thr Met Ser Glu Asn Asp Phe Lys His Thr Lys Ser
1               5                   10                  15

Phe Ile Ile

<210> SEQ ID NO 29
<211> LENGTH: 16
<212> TYPE: PRT
<213> ORGANISM: Artificial
<220> FEATURE:
<223> OTHER INFORMATION: Synthetic peptide

<400> SEQUENCE: 29

Ser Lys Val Thr Thr Met Ser Glu Asn Asp Phe Lys His Thr Lys Ser
1               5                   10                  15

<210> SEQ ID NO 30
<211> LENGTH: 19
<212> TYPE: PRT
<213> ORGANISM: Artificial
<220> FEATURE:
<223> OTHER INFORMATION: Synthetic peptide

<400> SEQUENCE: 30

Asn Tyr Ile Arg Thr Ser Glu Glu Gly Asp Phe Arg His Lys Ser Ser
1               5                   10                  15

Phe Val Ile
```

```
<210> SEQ ID NO 31
<211> LENGTH: 16
<212> TYPE: PRT
<213> ORGANISM: Artificial
<220> FEATURE:
<223> OTHER INFORMATION: Synthetic peptide

<400> SEQUENCE: 31

Asn Tyr Ile Arg Thr Ser Glu Glu Gly Asp Phe Arg His Lys Ser Ser
1               5                   10                  15

<210> SEQ ID NO 32
<211> LENGTH: 19
<212> TYPE: PRT
<213> ORGANISM: Artificial
<220> FEATURE:
<223> OTHER INFORMATION: Synthetic consensus peptide

<400> SEQUENCE: 32

Asn Gln Pro Ser Thr Met Ser Glu Asn Asp Phe Lys Gln Thr Lys Ser
1               5                   10                  15

Phe Ile Ile

<210> SEQ ID NO 33
<211> LENGTH: 19
<212> TYPE: PRT
<213> ORGANISM: Artificial
<220> FEATURE:
<223> OTHER INFORMATION: Synthetic consensus peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid

<400> SEQUENCE: 33

Ser Lys Val Thr Xaa Arg Glu Xaa Gly Glu Xaa Arg His Lys Ser Xaa
1               5                   10                  15

Xaa Leu Val

<210> SEQ ID NO 34
<211> LENGTH: 19
<212> TYPE: PRT
<213> ORGANISM: Artificial
<220> FEATURE:
<223> OTHER INFORMATION: Synthetic consensus peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(17)
<223> OTHER INFORMATION: Xaa can be any naturally occurring amino acid
```

```
<220> FEATURE:
<221> NAME/KEY: misc_feature
<222> LOCATION: (19)..(19)
<223> OTHER INFORMATION: Xaa can be any naturally occurring amino acid

<400> SEQUENCE: 34

Xaa Tyr Ile Arg Xaa Ser Xaa Xaa Xaa Xaa Xaa Xaa Xaa Xaa Xaa
1               5                   10                  15

Xaa Val Xaa

<210> SEQ ID NO 35
<211> LENGTH: 42
<212> TYPE: PRT
<213> ORGANISM: Artificial
<220> FEATURE:
<223> OTHER INFORMATION: Synthetic fragment of human JAM-A

<400> SEQUENCE: 35

Trp Phe Ala Tyr Ser Arg Gly His Phe Asp Arg Thr Lys Lys Gly Thr
1               5                   10                  15

Ser Ser Lys Lys Val Ile Tyr Ser Gln Pro Ser Ala Arg Ser Glu Gly
            20                  25                  30

Glu Phe Lys Gln Thr Ser Ser Phe Leu Val
        35                  40

<210> SEQ ID NO 36
<211> LENGTH: 43
<212> TYPE: PRT
<213> ORGANISM: Artificial
<220> FEATURE:
<223> OTHER INFORMATION: Synthetic fragment of murine JAM-A

<400> SEQUENCE: 36

Trp Phe Ala Tyr Ser Arg Gly Tyr Phe Glu Thr Thr Lys Lys Gly Thr
1               5                   10                  15

Ala Pro Gly Lys Lys Val Ile Tyr Ser Gln Pro Ser Thr Arg Ser Glu
            20                  25                  30

Gly Glu Phe Lys Gln Thr Ser Ser Phe Leu Val
        35                  40

<210> SEQ ID NO 37
<211> LENGTH: 40
<212> TYPE: PRT
<213> ORGANISM: Artificial
<220> FEATURE:
<223> OTHER INFORMATION: Synthetic fragment of human JAM-B

<400> SEQUENCE: 37

Cys Tyr Ala Gln Arg Lys Gly Tyr Phe Ser Lys Glu Thr Ser Phe Gln
1               5                   10                  15

Lys Ser Asn Ser Ser Ser Lys Ala Thr Thr Met Ser Glu Asn Asp Phe
            20                  25                  30

Lys His Thr Lys Ser Phe Ile Ile
        35                  40

<210> SEQ ID NO 38
<211> LENGTH: 40
<212> TYPE: PRT
<213> ORGANISM: Artificial
<220> FEATURE:
<223> OTHER INFORMATION: Synthetic fragment of murine JAM-B
```

```
<400> SEQUENCE: 38

Cys Tyr Ala Gln Arg Lys Gly Tyr Phe Ser Lys Glu Thr Ser Phe Gln
1               5                   10                  15

Lys Gly Ser Pro Ala Ser Lys Val Thr Thr Met Ser Glu Asn Asp Phe
            20                  25                  30

Lys His Thr Lys Ser Phe Ile Ile
        35                  40

<210> SEQ ID NO 39
<211> LENGTH: 47
<212> TYPE: PRT
<213> ORGANISM: Artificial
<220> FEATURE:
<223> OTHER INFORMATION: Synthetic fragment of human JAM-C

<400> SEQUENCE: 39

Cys Cys Ala Tyr Arg Arg Gly Tyr Phe Ile Asn Asn Lys Gln Asp Gly
1               5                   10                  15

Glu Ser Tyr Lys Asn Pro Gly Lys Pro Asp Gly Val Asn Tyr Ile Arg
            20                  25                  30

Thr Asp Glu Glu Gly Asp Phe Arg His Lys Ser Ser Phe Val Ile
        35                  40                  45

<210> SEQ ID NO 40
<211> LENGTH: 47
<212> TYPE: PRT
<213> ORGANISM: Artificial
<220> FEATURE:
<223> OTHER INFORMATION: Synthetic fragment of murine JAM-C

<400> SEQUENCE: 40

Cys Cys Ala Tyr Arg Arg Gly Cys Phe Ile Ser Ser Lys Gln Asp Gly
1               5                   10                  15

Glu Ser Tyr Lys Ser Pro Gly Lys His Asp Gly Val Asn Tyr Ile Arg
            20                  25                  30

Thr Ser Glu Glu Gly Asp Phe Arg His Lys Ser Ser Phe Val Ile
        35                  40                  45

<210> SEQ ID NO 41
<211> LENGTH: 54
<212> TYPE: PRT
<213> ORGANISM: Homo sapiens

<400> SEQUENCE: 41

Gly Phe Ile Lys Ile Cys Ser Val His Thr Pro Ser Ser Asn Pro Lys
1               5                   10                  15

Leu Pro Pro Pro Lys Pro Leu Pro Gly Thr Leu Lys Arg Arg Arg Pro
            20                  25                  30

Pro Gln Pro Ile Gln Gln Pro Pro Arg Gln Pro Arg Glu Tyr Gln
        35                  40                  45

Met Gly His Met Arg Arg
    50

<210> SEQ ID NO 42
<211> LENGTH: 135
<212> TYPE: PRT
<213> ORGANISM: Homo sapiens
```

```
<400> SEQUENCE: 42

Cys Val Asp Lys Lys Leu Asp Lys Gln Tyr Glu Ser Leu Ser Leu Phe
1               5                   10                  15

His His Ser Asn Ile Glu Met Leu Ser Ser Met Asp Ser Ala Ser Val
            20                  25                  30

Arg Ile Ile Lys Pro Phe Pro Ala Pro Gln Thr Pro Gly Arg Leu Gln
            35                  40                  45

Ala Leu Gln Pro Ala Ala Met Met Pro Pro Val Ser Ala Ala Pro Lys
        50                  55                  60

Leu Asp His Gln Arg Met Asp Thr Ile Gln Glu Asp Pro Ser Thr Asp
65                  70                  75                  80

Ser His Val Asp Asp Asp Gly Phe Glu Lys Asp Pro Phe Pro Asn Ser
                85                  90                  95

Ser Thr Ala Ala Lys Ser Phe Glu Asp Leu Thr Asp His Pro Val Thr
                100                 105                 110

Arg Ser Glu Lys Ala Ala Ser Phe Lys Leu Gln Arg Gln Ser Arg Val
            115                 120                 125

Asp Ser Lys Glu Thr Glu Cys
        130                 135

<210> SEQ ID NO 43
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 43
cuauuacacc ucuuaaagat t                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 44
gagucugacu ggacuuucut t                                              21
```